US009238606B1

(12) United States Patent
Penney et al.

(10) Patent No.: US 9,238,606 B1
(45) Date of Patent: *Jan. 19, 2016

(54) METHYL-IODIDE-FREE CARBONYLATION OF METHANOL TO ACETALDEHYDE

(71) Applicant: Eastman Chemical Company, Kingsport, TN (US)

(72) Inventors: Jonathan Michael Penney, Gray, TN (US); Andrew James Vetter, Kingsport, TN (US); David William Norman, Cary, NC (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/585,940

(22) Filed: Dec. 30, 2014

(51) Int. Cl.
    *C07C 45/49* (2006.01)
    *B01J 31/00* (2006.01)
    *B01J 31/24* (2006.01)

(52) U.S. Cl.
    CPC .............. *C07C 45/49* (2013.01); *B01J 31/24* (2013.01); *B01J 2231/34* (2013.01); *B01J 2531/10* (2013.01); *B01J 2531/845* (2013.01)

(58) Field of Classification Search
    CPC .. C07C 45/49; C07C 45/512; B01J 2531/845; B01J 31/0267; B01J 31/0268
    USPC ........................... 568/487; 502/162, 164, 169
    See application file for complete search history.

(56) References Cited

U.S. PATENT DOCUMENTS

| | | | |
|---|---|---|---|
| 2,727,902 | A | 12/1955 | Reppe et al. |
| 4,239,705 | A | 12/1980 | Pretzer et al. |
| 4,293,718 | A | 10/1981 | Gauthier-Lafaye et al. |
| 4,306,091 | A | 12/1981 | Gauthier-Lafaye et al. |
| 4,361,706 | A | 11/1982 | Habib et al. |
| 4,374,285 | A | 2/1983 | Lin et al. |
| 4,374,752 | A * | 2/1983 | Argento et al. ............... 502/162 |
| 4,389,532 | A * | 6/1983 | Larkins et al. ............... 568/487 |
| 4,400,551 | A | 8/1983 | Keim et al. |
| 4,484,002 | A | 11/1984 | Lin |
| 4,556,744 | A | 12/1985 | Griggs et al. |
| 4,954,665 | A | 9/1990 | Vidal |
| 5,770,541 | A | 6/1998 | Vanderspurt et al. |
| 5,908,807 | A | 6/1999 | Vanderspurt et al. |
| 5,939,352 | A | 8/1999 | Vanderspurt et al. |
| 6,034,141 | A | 3/2000 | Vanderspurt et al. |
| 7,700,192 | B2 | 4/2010 | Matthews et al. |
| 7,700,813 | B2 | 4/2010 | Kourtakis et al. |
| 7,745,672 | B2 | 6/2010 | Kourtakis et al. |
| 8,304,587 | B2 | 11/2012 | Warner et al. |
| 2007/0293695 | A1 | 12/2007 | Zoeller et al. |
| 2009/0247783 | A1 | 10/2009 | Zoeller et al. |

FOREIGN PATENT DOCUMENTS

| | | |
|---|---|---|
| CN | 101703926 A | 5/2010 |
| DE | 33 43 519 A1 | 6/1985 |
| DE | 35 06 714 A1 | 8/1986 |
| EP | 0 037 586 A1 | 10/1981 |
| FR | 697 726 | 1/1931 |
| FR | 697 727 | 1/1931 |
| FR | 697 896 | 1/1931 |
| JP | 2000 172854 A | 6/2000 |

OTHER PUBLICATIONS

Sharutin et al. Synthesis and Structure of Cobalt Complexes. Russian Journal of Inorganic Chemistry, 2011, vol. 56 (9), pp. 1384-1389.*
Bahrmann, Helmut; "Homologation—3.2 Special Catalysts and Processes"; Applied Homogeneous Catalysis Organometallic Compounds, vol. 2; pp. 902-914; 1996.
Dinka, P. et al.; "Reaction of methanol and n-propanol over hydrotalcite-like catalysts containing vanadium oxide"; Applied Clay Science, vol. 13; pp. 467-477; 1998.
Gauthier-Lafaye, Jean and Perron, Robert; "Chapter 4 Synthesis of acetaldehyde and ethanol"; methanol and carbonylation; pp. 39-96; 1987.
Gauthier-Lafaye, J. et al.; "Methanol Hydrocarbonylation into Acetaldehyde Catalyzed by Cobalt and Two Different Iodides"; Journal of Molecular Catalysis, vol. 17; pp. 339-347; 1982.
Girard, James W. et al.; "Technical Advantages of Vanadium SCR Systems for Diesel NOx Control in Emerging Markets"; SAE Int. J. Fuels Lubr, vol. 1, Issue 1; pp. 488-494; 2008.
Hong, H. et al.; "Study of $V_2 O_5$ Catalyst Deactivation for the Synthesis of Isobutyraldehyde from Methanol and Ethanol"; Chemical Engineering of Oil & Gas, vol. 37, No. 1; pp. 5-8; Feb. 2008 (original language and English abstract).
Hong, H. et al.; "Macrokinetics of Synthesis of Isobutyraldehyde from Methanol and Ethanol over $V_2O_5$ Catalyst"; Chemical Engineering of Oil & Gas, vol. 37, No. 5, pp. 370-372; Oct. 2008 (original language and English abstract).
Keim, W.; "Carbon monoxide: feedstock for chemicals, present and future"; Journal of Organometallic Chemistry, vol. 372; pp. 15-23; 1989.
Loevenich, Heinz and Röper, Michael; "Kinetic Studies of Methanol Homologation Using Cobalt—Phosphine—Iodine Catalysts"; $C_1$ Molecular Chemistry, vol. 1; pp. 155-170; 1984.
Mizoroki, Tsutomu et al.; "Further Study of Methanol Carbonylation Catalyzed by Cobalt, Rhodium, and Iridium Catalysts"; Bulletin of the Chemical Society of Japan, vol. 52, No. 2; pp. 479-482; 1979.
Moloy, Kenneth G. and Wegman, Richard W.; "Rhodium-Catalyzed Reductive Carbonylation of Methanol"; Organometallics, vol. 8; pp. 2883-2892; 1989.

(Continued)

*Primary Examiner* — Sikarl Witherspoon
(74) *Attorney, Agent, or Firm* — Jennifer R. Knight

(57) ABSTRACT

Disclosed is a process for the reductive carbonylation of methanol to produce acetaldehyde. The process includes conducting the reaction to produce acetaldehyde in the presence of a catalyst comprising a complex composed of cobalt, an onium cation and iodide in a ratio of 1:2:4, a phosphine ligand, and a phosphonium iodide. The reductive carbonylation reaction produces a crude reductive carbonylation product substantially free of methyl iodide.

16 Claims, No Drawings

(56) References Cited

OTHER PUBLICATIONS

Reddy, B. Mahipal et al.; "A Single-Step Synthesis of Isobutyraldehyde from Methanol and Ethanol over CuO—ZnO—$Al_2O_3$ Catalyst"; Journal Chemical Society, Chemical Commun.; pp. 997-998; 1992.

Reddy, B. M. et al.; "Vapour Phase Synthesis of Isobutyraldehyde from Methanol and Ethanol over Mixed Oxide Supported Vanadium Oxide Catalysts"; Res. Chem. Intermed., vol. 23, No. 8; pp. 703-713; 1997.

Sharutin, V. V. et al.; "Synthesis and Structure of Cobalt Complexes $[Me_3EtN]+_2 [CoI_4]^{2-}$ and $[Me_3BuN]+_2[CoI_4]^{2-}$"; Russian Journal of Inorganic Chemistry, vol. 56, No. 9; pp. 1384-1389; 2011.

Twigg, Martyn V.; "Progress and future challenges in controlling automotive exhaust gas emissions"; Applied Catalysis B: Environmental, vol. 70; pp. 2-15; 2007.

Wang, Fey-Long and Lin, Yi-Hsuan; "Alkylation of Acetaldehyde with Methanol over Titanium Oxide-Supported Vanadium Oxide"; Chemistry Letters; pp. 1867-1868; 1992.

Wang, Hui-Ying, et al.; "$V_2O_5/TiO_2$—$SiO_2$ Catalysts for the Synthesis of Isobutyraldehyde from Methanol and Ethanol"; Journal of Shenyang Institute of Chemical Technology, vol. 22, No. 3; pp. 200-203; Sep. 2008 (original language and English abstract).

Wender, Irving et al.; "Ethanol from Methanol"; Science, vol. 113; pp. 206-207; Feb. 23, 1951.

Wegman, Richard W. and Busby, David C.; "The Role of Phosphines and Solvents in $CoI_2$—Catalyzed Reductive Carbonylation of Methanol"; Journal of Molecular Catalysis, vol. 32; pp. 125-136; 1985.

Co-pending U.S. Appl. No. 14/585,884, filed Dec. 30, 2014; Penny et al.

Notice of Allowance dated Jun. 10, 2015 received in U.S. Appl. No. 14/585,884.

Co-pending U.S. Appl. No. 14/586,070, filed Dec. 30, 2014; Vetter et al.

Non-Final Office Action dated Jun. 9, 2015 received in U.S. Appl. No. 14/586,070.

Co-pending U.S. Appl. No. 14/585,915, filed Dec. 30, 2014; Vetter et al.

Co-pending U.S. Appl. No. 14/586,094, filed Dec. 30, 2014; Norman et al.

Notice of Allowance dated Jun. 11, 2015 received in U.S. Appl. No. 14/586,094.

Cuigai, Liu, et al.; "Effect of Double Promoters on $CuO/SiO_2$ Catalyst for Synthesis of Isobutyraldehyde from Methanol and Ethanol"; Petrochemical Technology; pp. 550-553; 2011 (original language and English abstract).

Wang, Fey-Long, et al.; "Alkylation of aldehydes with methanol over titanium oxide catalysts"; Catalysis Letters, vol. 42; pp. 155-160; 1996.

* cited by examiner

METHYL-IODIDE-FREE CARBONYLATION OF METHANOL TO ACETALDEHYDE

FIELD OF THE INVENTION

This invention relates to a process for the reductive carbonylation of methanol to produce acetaldehyde. The invention relates to the reductive carbonylation of methanol without the need to use methyl iodide as a co-catalyst. Specifically the invention relates to a process of conducting the reductive carbonylation reaction in the presence of a catalyst composition comprising a cobalt/onium cation/iodide complex, a phosphine ligand, and a phosphonium iodide such that there is less than one weight percent methyl iodide in the crude reductive carbonylation product.

BACKGROUND OF THE INVENTION

Cobalt can catalyze the formation of acetaldehyde from methanol, carbon monoxide, and hydrogen, a reaction known as methanol reductive carbonylation. For example, it was disclosed by Wender et al., *Science*, 113, (1951), 206-207, that a cobalt carbonyl catalyst system could be used. However, the product of the disclosed process was primarily ethanol, together with a small amount of acetaldehyde. It was later shown that the addition of iodide to a cobalt-containing catalyst system increased the amount of acetaldehyde produced. Iodide is typically added as a co-catalyst (also commonly referred to as a promoter) to the reaction in a form such as hydrogen iodide (a strong acid), methyl iodide, elemental iodide, or as an iodide salt such as lithium iodide or sodium iodide.

Addition of commonly-used industrial iodide co-catalysts in these reactions often leads to formation of dimethyl ether as well as free methyl iodide in the crude reductive carbonylation product. Methyl iodide is an undesirable co-product due to the difficulty in separating it from the aldehyde product as well as its toxicity. Current methanol reductive carbonylation processes carefully balance the amount of iodide containing compounds added to the reaction to obtain optimized reaction rate and conversion while limiting dimethyl ether and methyl iodide formation.

There is a need for an improved catalyst system which will allow reasonable reductive carbonylation reaction rates as well as little to no methyl iodide in the crude reductive carbonylation product. There is also a need for an inexpensive catalyst for the carbonylation of alcohol that can replace the typical rhodium catalyst or iridium/ruthenium catalyst while producing a substantially methyl iodide free crude reductive carbonylation product.

SUMMARY OF THE INVENTION

The present invention provides in a first embodiment a catalyst composition comprising a complex of cobalt, iodide, and an onium cation or an alkali metal cation of the general formula $Y_2CoI_4$. Y is the onium cation or alkali metal cation. The catalyst composition also comprises a phosphine ligand of the general formula

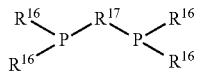

The phosphorus atoms P are bridged by 2 to 6 atoms of $R^{17}$. $R^{17}$ is selected from the group consisting of a substituted or unsubstituted alkylene, cycloalkylene, arylene, and biarylene, each having up to 22 carbon atoms. A heteroatom, optionally, can substitute for one or more of the carbon atoms. The heteroatom can be nitrogen, oxygen, sulfur, phosphorus or mixtures thereof. $R^{16}$ can be substituted or unsubstituted alkyl, alkoxy, cycloalkyl, aryl, or aryloxy, each having up to 20 carbon atoms. The catalyst composition also comprises a phosphonium iodide.

The present invention provides in a second embodiment a process for the preparation of a crude reductive carbonylation product comprising contacting hydrogen, carbon monoxide, and methanol in the presence of a catalyst composition to form the crude reductive carbonylation product. The crude reductive carbonylation product comprises acetaldehyde equivalents in a higher mole percent than acetic acid equivalents or ethanol equivalents, each based on the total moles of the acetaldehyde equivalents, the acetic acid equivalents, and the ethanol equivalents. The catalyst composition comprises a complex of cobalt, iodide, and an onium cation of the general formula $Y_2CoI_4$, wherein Y is the onium cation of the general formula (I) or (II)

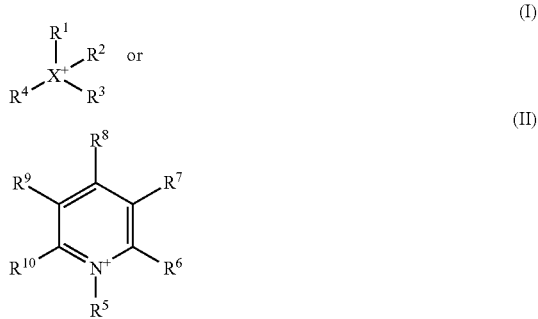

wherein X is phosphorus (P), $R^1$ is methyl, and $R^2$, $R^3$, and $R^4$ are independently selected from alkyl having up to 12 carbon atoms and aryl, wherein the aryl is selected from only one of the group consisting of phenyl, tolyl, xylyl, and mesityl; $R^5$ is methyl and $R^6$, $R^7$, $R^8$, $R^9$, and $R^{10}$ are hydrogen. The catalyst composition also comprises a phosphine ligand selected from the group consisting of 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and 1,3-bis(diphenylphosphino)cyclobutane. The catalyst composition also comprises a phosphonium iodide. The crude reductive carbonylation product comprises less than 1 weight percent of methyl iodide, based on the total weight of the crude reductive carbonylation product.

DETAILED DESCRIPTION

The present invention provides in a first embodiment a catalyst composition comprising a complex of cobalt, iodide, and an onium cation or an alkali metal cation of the general formula $Y_2CoI_4$. Y is the onium cation or alkali metal cation. The catalyst composition also comprises a phosphine ligand of the general formula

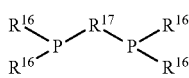

The phosphorus atoms P are bridged by 2 to 6 atoms of $R^{17}$. $R^{17}$ is selected from the group consisting of a substituted or unsubstituted alkylene, cycloalkylene, arylene, and biarylene, each having up to 22 carbon atoms. A heteroatom, optionally, can substitute for one or more of the carbon atoms. The heteroatom can be nitrogen, oxygen, sulfur, phosphorus or mixtures thereof. $R^{16}$ can be substituted or unsubstituted alkyl, alkoxy, cycloalkyl, aryl, or aryloxy, each having up to 20 carbon atoms. The catalyst composition also comprises a phosphonium iodide.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

It is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

As used herein, the singular forms "a", "an", and "the" include plural referents unless the context clearly dictates otherwise. For example, reference to a complex of cobalt iodide and an onium cation is intended to include multiple complexes of cobalt iodide and onium cations.

As used herein the term "and/or", when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "crude reductive carbonylation product", as used herein, refers to the reaction products of carbon monoxide, methanol, and hydrogen. The crude reductive carbonylation product comprises the many different compounds produced under carbonylation conditions. The crude reductive carbonylation product is the liquid effluent directly exiting the carbonylation reactor, before any separation of the homogeneous catalyst or other liquid compounds. The crude reductive carbonylation product comprises acetaldehyde, acetic acid, and/or ethanol, unreacted methanol, and other byproducts, as well as the catalyst. The term "acetaldehyde equivalents", as used herein, refers to the methanol reductive carbonylation products and byproducts containing at least one aldehyde group. The term "acetic acid equivalents", as used herein refers, to the common products and byproducts containing at least one acid group. The term "ethanol equivalents", as used herein, refers to the common products and byproducts containing at least one alcohol group. The most common acetaldehyde equivalents, acetic acid equivalents, and ethanol equivalents are listed in the specification.

The term "catalyst", as used herein, has its typical meaning to one skilled in the art as a substance that increases the rate of chemical reactions without being consumed. The term "catalyst composition", as used herein, refers to a catalyst comprising a cobalt complex, a phosphine ligand, and phosphonium iodide.

The term "complex", "coordination complex" and "metal complex" as used herein, are equivalent terms which have their typical meaning to one skilled in the art as a metal ion and a surrounding array of bound molecules.

The term "onium cation", as used herein, refers to a cation selected from quaternary atoms or radicals such as quaternary ammonium, quaternary phosphonium, trialkyl sulfonium, and alkylated sulfoxide. The onium cation can also be of N-alkylated pyridinium. The term "onium salt", as used herein refers to a salt containing an onium cation. One skilled in the art will recognize that the disclosure of any onium salt necessarily and simultaneously discloses the corresponding onium cation.

The term "alkali metal cation", as used herein, refers to a group one element of the periodic table excluding hydrogen having at least one more proton than electron.

The term "phosphine ligand", as used herein, refers to an organic compound composed of hydrocarbyl groups covalently bound to one or more phosphorus atoms in the +3 oxidation state such that the lone pair of at least one of the phosphorus atoms binds the cobalt when dissolved in solution with cobalt. Such ligands are commonly referred to as tertiary phosphine since the phosphorus atom is substituted by three groups.

The term "bridged by" a number of atoms, as used herein, refers to the smallest number of consecutive atoms in a path between two atoms, specifically the two phosphorus atoms. For example, 1,3-bis(diphenyl phosphino)propane is bridged by 3 carbon atoms, 1,4-bis(diphenyl phosphino) butane is bridged by 4 carbon atoms, 1,2-bis(diphenylphosphino)benzene is bridged by 2 carbon atoms, bis(diphenylphosphinomethyl)biphenyl is bridged by 6 carbon atoms, and 1,1,1-tris(diphenylphosphinomethyl)ethane is bridged by 3 carbon atoms.

The term "alkylene", as used herein, refers to an alkylenediyl group having free valences at each group end to bond to the two phosphorus atoms. The terms "cycloalkylene", "arylene", and "biarylene" are used in a like manner. When the term "substituted or unsubstituted" is followed by a listing of hydrocarbon groups, the term is intended to modify each group. When a listing of hydrocarbon groups is followed by the term, "each having up to [a number of] carbon atoms", the term is intended to modify each group. The term "substituted", as used herein, has its usual meaning in the art, as in the hydrogen on the hydrocarbon may be substituted with the stated group. The term "heteroatom", as used herein, has its usual meaning in the art as an atom, such as nitrogen, oxygen, sulfur, or phosphorous, substituted for a carbon atom in a hydrocarbon.

The term "phosphonium iodide", as used herein, refers to quaternary phosphonium cation with an iodide anion.

The term "higher mole percent", as used herein, refers to a larger number of moles of one component than another component in a mixture. For example, if a crude reductive carbonylation product contains 60 mole percent acetaldehyde equivalents, 30 mole percent acetic acid equivalents, and 10 mole percent ethanol equivalents, on a total acetaldehyde equivalents, acetic acid equivalents, and ethanol equivalents basis, then the crude reductive carbonylation product has a higher mole percent of acetaldehyde equivalents than either of acetic acid equivalents or ethanol equivalents. In the specific example, the crude reductive carbonylation product has 60−30=30 mole percent higher acetaldehyde equivalents than acetic acid equivalents and 60−10=50 mole percent higher acetaldehyde equivalents than ethanol equivalents.

The catalyst composition of the present invention can be used, for example, in the reductive carbonylation of methanol to acetaldehyde. The catalyst composition comprises a complex of cobalt, iodide, and an onium cation or an alkali metal cation of the general formula $Y_2CoI_4$, a phosphine ligand, and a phosphonium iodide.

The complex can be readily synthesized by those skilled in the art. For example, an onium iodide salt or alkali metal iodide salt can be reacted with cobalt(II) iodide as illustrated in the reaction below.

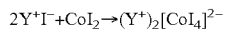

$2Y^+I^- + CoI_2 \rightarrow (Y^+)_2[CoI_4]^{2-}$

When an onium salt is used to produce the complex, the onium salt can comprise an onium cation selected from quaternary atoms or radicals such as quaternary ammonium, quaternary phosphonium, trialkyl sulfonium, and alkylated sulfoxide. The onium salt compound can be functional and includes protonated forms of the atoms or radicals, especially protonated forms of various tertiary amines and tertiary phosphines. The onium salt can contain any number of carbon atoms, e.g., up to about 60 carbon atoms, and also can contain one or more heteroatoms. The tri- and tetra-alkyl quaternary ammonium and phosphonium salts typically contain a total of about 5 to 40 carbon atoms. One skilled in the art understands that the listing of the onium salts simultaneously gives a listing of the onium cations (e.g., if onium salt methyltriphenylphosphonium iodide is disclosed, then onium cation methyltriphenylphosphonium is also disclosed).

Examples of an alkali metal cation include cations of lithium, sodium, potassium, rubidium and cesium. In one aspect, the alkali metal cation can be lithium, sodium, potassium, rubidium, or cesium. In another aspect, the alkali metal cation can be lithium, sodium, or potassium.

Examples of quaternary ammonium and phosphonium salts include salts having onium cations of the general formula (I)

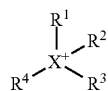

(I)

wherein X can be phosphorus (P) or nitrogen (N) and wherein $R^1$, $R^2$, $R^3$, and $R^4$ independently can be substituted or unsubstituted alkyl having up to 20 carbon atoms, substituted or unsubstituted cycloalkyl having 5 to 20 carbon atoms, or substituted or unsubstituted aryl having 6 to 20 carbon atoms.

In one aspect, X can be phosphorus (P) or nitrogen (N), $R^1$ is methyl, and $R^2$, $R^3$, and $R^4$ can be independently an alkyl having up to 12 carbons or an aryl. When $R^2$, $R^3$, and/or $R^4$ are aryl, the aryl is selected from only one of the group consisting of phenyl, tolyl, xylyl, and mesityl.

The quaternary ammonium salts can also be selected from salts of aromatic, heterocyclic onium cations having the general formula (II) or (III)

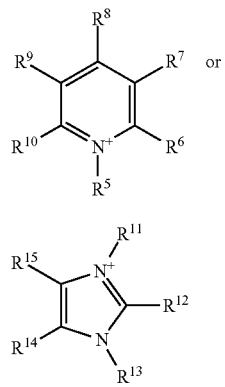

wherein at least one ring atom is a quaternary nitrogen atom and $R^6$, $R^7$, $R^8$, $R^9$, $R^{10}$, $R^{12}$, $R^{14}$, and $R^{15}$ are independently selected from hydrogen, substituted or unsubstituted alkyl having up to 20 carbon atoms, substituted or unsubstituted cycloalkyl having 5 to 20 carbon atoms, and substituted or unsubstituted aryl having 6 to 20 carbon atoms; and $R^5$, $R^{11}$, and $R^{13}$ are independently selected from substituted or unsubstituted alkyl having up to 20 carbon atoms, substituted or unsubstituted cycloalkyl having 5 to 20 carbon atoms, and substituted or unsubstituted aryl having about 6 to about 20 carbon atoms. In one aspect, $R^5$ is methyl and $R^6$, $R^7$, $R^8$, $R^9$, and $R^{10}$ are hydrogen.

Examples of specific ammonium salts include tetrapentylammonium iodide, tetrahexylammonium iodide, tetraoctylammonium iodide, tetradecylammonium iodide, tetradodecylammonium iodide, tetrapropylammonium iodide, tetrabutylammonium iodide, methyltrioctylammonium iodide, methyltributylammonium iodide, N-octyl-quinuclidinium iodide, N,N'-dimethyl-N,N'-dihexadecylpiperazinium diiodide, dimethyl-hexadecyl-[3-pyrrolidinylpropyl]ammonium iodide, N,N,N,N',N',N'-hexa(dodecyl)octane-1,8-diammonium diiodide, N,N,N,N',N',N'-hexa(dodecyl)butane-1,4-diammonium diiodide; imidazolium iodides such as 1-butyl-3-methylimidazolium iodide, 1,3-dimethylimidazolium iodide, 1,3,4-trimethyl-imidazolium iodide, 1,2,3,4,5-pentamethylimidazolium iodide; pyridinium iodides such as N-octylpyridinium iodide, N-methylpyridinium iodide, N-methyl-2-picolinium iodide, N-methyl-3-picolinium iodide, N-methyl-4-picolinium iodide, N-methyl-5-ethyl-2-methyl-pyridinium iodide, N-methyl-3,4-lutidinium iodide; N-methyl quinolinium iodide, N-methyl isoquinolinium iodide or mixtures thereof. Preferred quaternary ammonium iodides include 1-butyl-3-methylimidizolium iodide, N-methyl pyridinium iodide, N-methyl-2-methyl pyridinium iodide, N-methyl-3-methyl pyridinium iodide, N-methyl-4-methyl pyridinium iodide, or 1,3-dimethylimidazolium iodide.

Exemplary phosphonium salts include tetraoctylphosphonium iodide, tetrabutylphosphonium iodide, triphenyl(hexyl) phosphonium iodide, triphenyl(octyl)phosphonium iodide, tribenzyl(octyl)phosphonium iodide, tribenzyl(dodecyl) phosphonium iodide, triphenyl(decyl)phosphonium iodide, triphenyl(dodecyl)phosphonium iodide, tetrakis(2-methylpropyl)phosphonium iodide, tris(2-methylpropyl)(butyl) phosphonium iodide, triphenyl(3,3-dimethylbutyl)phosphonium iodide, triphenyl(3-methylbutyl)phosphonium iodide, tris(2-methylbutyl)(3-methylbutyl)phosphonium iodide, triphenyl[2-trimethylsilylethyl]phosphonium iodide, tris(p-chlorophenyl)-(dodecyl)phosphonium iodide, hexyltris(2,4,6-trimethylphenyl)phosphonium iodide, tetradecyltris(2,4,6-trimethylphenyl)phosphonium iodide, dodecyltris(2,4,6-trimethylphenyl)phosphonium iodide, methyltrioctylphosphonium iodide, methyltributylphosphonium iodide, methyltricyclohexylphosphonium iodide, and the like. Preferred phosphonium iodides include methyltriphenylphosphonium iodide, methyltributylphosphonium iodide, or methyltrioctylphosphonium iodide.

In one aspect, the onium cation can be of the general formula (I) or (II)

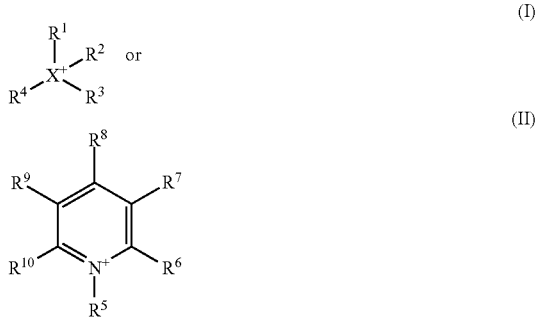

X can be phosphorus (P) or nitrogen (N), $R^1$ is methyl, and $R^2$, $R^3$, and $R^4$ independently can be an alkyl having up to 12 carbon atoms or an aryl, wherein the aryl is selected from only one of the group consisting of phenyl, tolyl, xylyl, and mesityl; $R^5$ is methyl and $R^6$, $R^7$, $R^8$, $R^9$, and $R^{10}$ are hydrogen. In another aspect, the onium cation is of formula (I), where X is phosphorus (P), $R^1$ is methyl, and $R^2$, $R^3$, and $R^4$ independently can be an alkyl having up to 12 carbons or an aryl. When $R^2$, $R^3$, and/or $R^4$ are aryl, the aryl groups are the same and can be phenyl, tolyl, xylyl, or mesityl.

In one aspect, the onium cation can be methyltriphenylphosphonium, methyltributylphosphonium, methyltrioctylphosphonium, or 1-methylpyridinium. In another aspect, the onium cation can be methyltriphenylphosphonium, methyltributylphosphonium, or 1-methylpyridinium. In another aspect, the onium cation can be methyltriphenylphosphonium or 1-methylpyridinium. In one aspect, the complex can be bis(methyltriphenylphosphonium) cobalt tetraiodide, bis(methyltributylphosphonium) cobalt tetraiodide, or bis(1-methylpyridinium) cobalt tetraiodide.

In one aspect of the invention, the onium salt can be generated from polymers containing a quaternary or quaternizable phosphine or amine. The onium salt polymer may be derived in whole or part from (or containing polymerized residues of) 2- or 4-vinyl-N-alkylpyridinium iodide or 4-(trialkyl-ammonium)styrene iodide. For example, a variety of 4-vinyl pyridine polymers and copolymers are available, and may be quaternized or protonated with alkyl iodide or hydrogen iodide to generate heterogeneous onium salts. Further, polymers of N-methyl-4-vinylpyridinium chloride are commercially available and may be used as-is or are preferably exchanged with iodide by well-known means to form the iodide salt. The heterogeneous onium compound may comprise (1) an onium salt compound deposited on a catalyst support material or (2) of a polymeric material containing quaternary nitrogen groups. Examples of such polymeric onium compounds include polymers and co-polymers of vinyl monomers which contain quaternary nitrogen (ammonium) groups. Polymers and copolymers derived from 2- and 4-vinyl-N-alkylpyridinium iodide, e.g., poly(4-vinyl-N-methylpyridinium iodide), are specific examples of such polymeric onium salt compounds. In this aspect, the onium cation would be a heterogeneous component in the reaction mixture.

The catalyst composition of the invention comprises a cobalt complex, a phosphine ligand, and a phosphonium iodide. The phosphine ligand is a multidentate compound containing at least two bridged phosphorus atoms. The phosphine ligand can be of the general formula

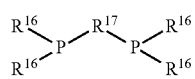

The phosphorus atoms P are bridged by 2 to 6 atoms of $R^{17}$. $R^{17}$ can be a substituted or unsubstituted alkylene, cycloalkylene, arylene and/or biarylene, each having up to 22 carbon atoms. $R^{17}$ can optionally contain one or more heteroatoms. The heteroatom can be nitrogen, oxygen, sulfur, phosphorus, or mixtures thereof. $R^{16}$ is a substituted or unsubstituted alkyl, alkoxy, cycloalkyl, aryl, and/or aryloxy, each having up to 20 carbon atoms.

The phosphorus atoms P are bridged by 2 to 6 atoms which means that the shortest molecular path between the two phosphorus atoms contains 2 to 6 atoms. These 2 to 6 atoms are referred to as bridging atoms. The bridging atoms can be carbon and/or heteroatom selected from nitrogen, oxygen, sulfur, phosphorus or mixtures thereof.

In one example, $R^{17}$ can be a straight- or branch-chain hydrocarbon radical containing 2 to 6 bridging atoms, where the bridging atoms can be substituted, for example, with alkyl, alkoxy, aryl, dialkylphosphinomethyl, diarylphosphino, or diarylphosphinomethyl.

In another aspect, $R^{17}$ can be arylene or biarylene. The arylene or biarylene can be substituted, for example, with methyl, ethyl, propyl, iso-propyl, butyl, iso-butyl, methoxy, ethoxy, propoxy, iso-propoxy, butoxy, iso-butoxy, phenoxy, nitro, chloro, fluoro, trifluoromethyl. In another aspect, the arylene or biarylene can be substituted with methyl, ethyl, propyl, or iso-propyl.

In one aspect, $R^{16}$ can be a substituted alkyl, alkoxy, cycloalkyl, aryl, or aryloxy wherein the substituted group can be, for example, methyl, ethyl, propyl, iso-propyl, butyl, iso-butyl, methoxy, ethoxy, propoxy, iso-propoxy, butoxy, iso-butoxy, phenoxy, nitro, chloro, fluoro, or trifluoromethyl. In another aspect, the substituted group can be methyl, ethyl, propyl, or iso-propyl.

In one aspect, $R^{16}$ is chosen from phenyl, naphthyl, anthryl, tetrahydronaphthyl, or octahydronaphthyl each of which can be substituted with alkyl, alkoxy, aryl, aryloxy, halogen, or nitro. In one aspect, $R^{16}$ can be methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, or mesityl-oxy Without representing an exhaustive list, specific examples of multidentate phosphine ligands useful in the present invention include 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane; 1,5-bis(diphenylphosphino)pentane; 1,2-bis(dicyclohexylphosphino)ethane; 1,3-bis(dicyclohexylphosphino)propane; 1,4-bis(dicyclohexylphosphino)butane; 1,5-bis(dicyclohexylphosphino)pentane; 1,6-bis(dicyclohexylphosphino)hexane; 1,2-bis(dimethylphosphino)ethane; 1,3-bis(dimethylphosphino)propane; 1,4-bis(dimethylphosphino)butane; 1,5-bis(dimethylphosphino)pentane; 1,6-bis(dimethylphosphino)hexane; 1,2-bis(diisopropylphosphino)ethane; 1,3-bis(diisopropylphosphino)propane; 1,4-bis(diisopropylphosphino)butane; 1,2-bis(di-tert-butylphosphine)ethane; 1,3-bis(di-tert-butylphosphino)propane; 1,4-bis(di-tert-butyl phosphine)butane; 2,2'-bis(diphenylphosphino)-1,1'-binaphthalene; 2,2'-bis(diphenylphosphino)-1,1'-biphenyl; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and/or 1,3-bis(diphenylphosphino)cyclobutane.

In one aspect the phosphine ligand can be chosen from 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and/or 1,3-bis(diphenylphosphino)cyclobutane.

In one aspect, the phosphine ligand can be chosen from 1,3-bis(diphenylphosphino)propane; 1,1,1,-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and/or 1,3-bis(diphenylphosphino)cyclobutane.

In one aspect the phosphine ligand can be 1,2-bis(diphenylphosphino)ethane; 1,4-bis(diphenylphosphino)butane; 1,6-bis(diphenylphosphino)hexane; 1,2-bis(diphenylphosphino)benzene; bis(diphenylphosphinomethyl)biphenyl; 1,3-bis(diphenylphosphino)propane; 1,1,1-tris(diphenylphosphinomethyl)ethane; and/or 1,1,1-tris(diethylphosphinomethyl)ethane. In one aspect, the phosphine ligand can be 1,3-bis(diphenylphosphino)propane, 1,1,1,-tris(diphenylphosphinomethyl)ethane; and/or 1,1,1-tris(diethylphosphinomethyl)ethane.

In one aspect, the phosphorus atoms are bridged by saturated or unsaturated alkylene containing three carbon atoms. The phosphine ligand can be of the general formula

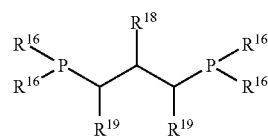

In one aspect, $R^{18}$ can be a hydrogen radical or a hydrocarbon radical having up to 17 carbon atoms. The hydrocarbon radical can be substituted with alkyl, alkoxy, cycloalkyl aryl, aryloxy dialkylphosphinomethyl, diarylphosphinomethyl, or mixtures thereof. In another aspect, $R^{18}$ can be a hydrogen radical, methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, mesityl-oxy, dimethylphosphinomethyl, diethylphosphinomethyl, di-n-propylphosph inomethyl, di-iso-propylphosphinomethyl, di-n-butyl phosph inomethyl, di-iso-butylphosphinomethyl, di-tert-butylphosphinomethyl, dimethoxyphosphinomethyl, diethoxyphosphinomethyl, di-n-propoxyphosphinomethyl, di-iso-propoxyphosphinomethyl, di-n-butoxyphosph inomethyl, di-iso-butoxyphosph inomethyl, di-tert-butoxyphosphinomethyl diphenylphosphinomethyl, ditolylphosphinomethyl, or dixylylphosphinomethyl.

$R^{19}$ can be a hydrogen radical or a substituted or unsubstituted alkyl, alkoxy, cycloalkyl, aryl, and aryloxy, each having up to 8 carbon atoms. In one aspect, $R^{19}$ can be a hydrogen radical or a substituted or unsubstitued alkyl. In one aspect, $R^{19}$ can be a hydrogen radical.

In one aspect $R^{16}$ can be methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, or mesityl-oxy.

In one aspect, $R^{16}$ or $R^{18}$ can be unsubstituted aryl, alkyl, cycloalkyl, alkoxy, or aryloxy substituted, for example, with groups selected from methyl, ethyl, propyl, iso-propyl, butyl, iso-butyl, methoxy, ethoxy, propoxy, iso-propoxy, butoxy, iso-butoxy, phenoxy, nitro, chloro, fluoro, and/or trifluoromethyl.

In one aspect, $R^{16}$ or $R^{18}$ can be aryl groups chosen from phenyl, naphthyl, anthryl, tetrahydronaphthyl, and/or octahydronaphthyl with any of the groups substituted with alkyl, alkoxy, aryl, aryloxy, halogen, and/or nitro.

In one aspect, the phosphorus atoms are bridged by saturated or unsaturated alkylene containing three carbon atoms. The phosphine ligand can be of the general formula

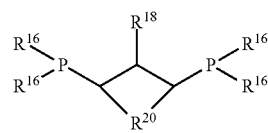

$R^{20}$ can be a substituted or unsubstituted alkyl having up to 8 carbon atoms, forming a cycloalkyl group between the phosphorus atoms. $R^{18}$ is a hydrogen radical and $R^{16}$ is selected from the group consisting of methyl, ethyl, n-propyl, iso-propyl, n-butyl, iso-butyl, tert-butyl, methoxy, ethoxy, n-propoxy, iso-propoxy, n-butoxy, iso-butoxy, tert-butoxy, phenyl, tolyl, xylyl, mesityl, phenoxy, tolyl-oxy, xylyl-oxy, and mesityl-oxy.

The catalyst composition of the invention comprises a cobalt complex, a phosphine ligand, and a phosphonium iodide. The phosphonium iodide is not particularly limited and can be the same or different from the phosphonium iodide used to produce the cobalt complex. The phosphonium iodide can be selected from methyltriphenylphosphonium iodide, methyltributylphosphonium iodide, methyltrioctylphosphonium iodide, butyltridodecylphosphonium iodide, tetraoctylphosphonium iodide, tetrabutylphosphonium iodide, triphenyl(hexyl)-phosphonium iodide, triphenyl(octyl)phosphonium iodide, tribenzyl(octyl)phosphonium iodide, tribenzyl(dodecyl)phosphonium iodide, triphenyl(decyl)phosphonium iodide, triphenyl(dodecyl)-phosphonium iodide, tetrakis(2-methylpropyl)phosphonium iodide, tris(2-methylpropyl)-(butyl)phosphonium iodide, triphenyl(3,3-dimethylbutyl)-phosphonium iodide, triphenyl(3-methylbutyl)phosphonium iodide, tris(2-methylbutyl)-(3-methyl-butyl)-phosphonium iodide, triphenyl[2-trimethylsilylethyl]phosphonium iodide, tris(p-chlorophenyl)-(dodecyl)phosphonium iodide, hexyltris(2,4,6-trimethyl-phenyl)phosphonium iodide, tetradecyltris(2,4,6-trimethyl-phenyl)phosphonium iodide, dodecyltris(2,4,6-trimethylphenyl)phosphonium iodide, methyltrioctylphosphonium iodide, methyltributylphosphonium iodide, and methyltricyclohexylphosphonium iodide. In another aspect, the phosphonium iodide can be selected from methyltriphenylphosphonium iodide, methyltributylphosphonium iodide, methyltrioctylphosphonium iodide, and butyltridodecylphosphonium iodide. In another aspect, the phosphonium iodide can be selected from methyltriphenylphosphonium iodide, methyltributylphosphonium iodide, and methyltrioctylphosphonium iodide. In yet another aspect, the phosphonium iodide comprises methyltriphenylphosphonium.

In one aspect, the onium cation can be methyltriphenylphosphonium, methyltributylphosphonium, methyltrioctylphosphonium, and/or 1-methylpyridinium; the phosphine ligand can be 1,3-bis(diphenylphosphino)propane, 1,1,1-tris(diphenylphosphinomethyl)ethane, and/or 1,1,1-tris(diethylphosphinomethyl)ethane; and the phosphonium iodide can be methyltriphenylphosphonium iodide, methyltributylphosphonium iodide, and/or methyltrioctylphosphonium. In one aspect, the onium cation can be methyltriphenylphosphonium, the phosphine ligand can be 1,3-bis(diphenylphosphino)propane, and the phosphonium iodide can be methyltriphenylphosphonium iodide.

In one aspect, the molar ratio of the phosphine ligand to the cobalt (phosphine ligand:cobalt) ranges from 0.025:1 to 2:1. In other examples, the molar ratio of phosphine ligand to cobalt (phosphine ligand:cobalt) ranges from 0.025:1 to 0.5:1 or 0.025:1 to 1:1 or 0.025:1 to 1.5:1 or 0.1:1 to 1:1 or 0.1:1 to 0.1:1.5, or 1:1 to 2:1. In one aspect, the molar ratio of the phosphonium iodide to the cobalt (phosphonium iodide:cobalt) ranges from 0.1:1 to 50:1. In other examples, the molar ratio of phosphonium iodide to cobalt (phosphonium iodide:cobalt) ranges from 0.1:1 to 20:1 or 0.1:1 to 10:1 or 0.1:1 to 5:1 or 1:1 to 50:1 or 1:1 to 20:1 or 1:1 to 10:1 or 1:1 to 1.5:1.

The catalyst composition can further comprise a solvent. The solvent is not particularly limiting so long as it is inert under reaction conditions. Other considerations in the selection of a solvent are reactants and products for the catalyst composition use, unit price, corrosion, and the like. When using the catalyst composition for the reductive carbonylation of methanol, methanol can be the solvent.

The catalyst composition of the first embodiment can be used in a process for the reductive carbonylation of methanol to acetaldehyde. A second embodiment of our invention is of process for the preparation of a crude reductive carbonylation product comprising contacting hydrogen, carbon monoxide, and methanol in the presence of a catalyst composition to form the crude reductive carbonylation product. The crude reductive carbonylation product comprises acetaldehyde equivalents in a higher mole percent than acetic acid equivalents or ethanol equivalents, each based on the total moles of the acetaldehyde equivalents, the acetic acid equivalents, and the ethanol equivalents. The catalyst composition comprises a complex of cobalt, iodide, and an onium cation of the general formula $Y_2CoI_4$, where Y represents the onium cation. The onium cation is of the general formula (I) or (II)

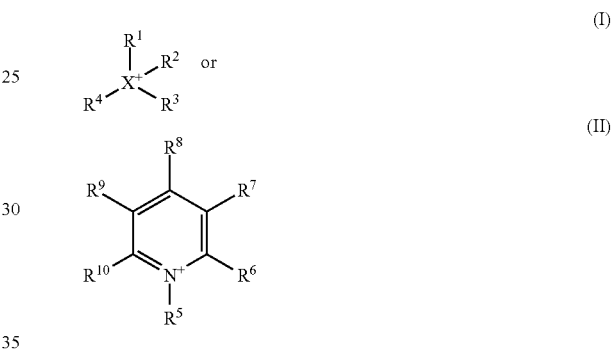

For formula (I), X is phosphorus (P) and $R^1$ is methyl. $R^2$, $R^3$, and $R^4$ are independently selected from alkyl having up to 12 carbons and aryl. When $R^2$, $R^3$, and/or $R^4$ are aryl, each aryl is the same, and can be phenyl, tolyl, xylyl, or mesityl. For formula (II), $R^5$ is methyl and $R^6$, $R^7$, $R^8$, $R^9$, and $R^{10}$ are hydrogen. The catalyst composition also comprises a phosphine ligand. The phosphine ligand can be 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and/or 1,3-bis(diphenylphosphino)cyclobutane. The catalyst composition further comprises a phosphonium iodide. The crude reductive carbonylation product comprises less than 1 weight percent of methyl iodide.

It is understood that the descriptions herein above regarding, the catalyst composition, the onium cation/salts and alkali cations/salts, the phosphine ligands, the phosphonium iodide, the molar ratio of phosphine ligand to cobalt, and the molar ratio of phosphonium iodide to cobalt apply equally well to the second embodiment.

Methanol is contacted with carbon monoxide and hydrogen to produce a crude reductive carbonylation product comprising acetaldehyde equivalents in a higher mole percent than acetic acid equivalents or ethanol equivalents, each based on the total moles of acetaldehyde equivalents, acetic acid equivalents, and ethanol equivalents.

The total moles of acetaldehyde equivalents are determined as the sum of the moles of reductive carbonylation product compounds that have at least one aldehyde group, with the number of moles of each compound multiplied by the number of aldehyde groups in the compound. The acetaldehyde equivalents are the sum of the moles Acetaldehyde+3*moles Paraldehyde+moles Acetaldehyde dimethyl acetal+moles Acetaldehyde methyl ethyl acetal+moles Acetaldehyde diethyl acetal. The total moles of acetic acid equivalents and ethanol equivalents are determined in the same manner. The acetaldehyde equivalents, acetic acid equivalents, and ethanol equivalents are listed below.

| Acetaldehyde Equivalents | Acetic Acid Equivalents | Ethanol Equivalents |
|---|---|---|
| Acetaldehyde | Acetic acid | Ethanol |
| Acetaldehyde dimethyl acetal | Methyl acetate | Acetaldehyde diethyl acetal |
| Acetaldehyde methyl ethyl acetal | Ethyl acetate | Acetaldehyde methyl ethyl acetal |
| Acetaldehyde diethyl acetal | | Diethyl ether |
| Paraldehyde | | Methyl ethyl ether |
| | | Ethyl acetate |

The hydrogen and carbon monoxide contacted with methanol can be obtained from typical sources that are well known in the art. For example, the carbon monoxide and hydrogen can be provided by any of a number of methods known in the art including steam or carbon dioxide reforming of carbonaceous materials such as natural gas or petroleum derivatives; partial oxidation or gasification of carbonaceous materials, residuum, bituminous, sub bituminous, and anthracitic coals and cokes; lignite; oil shale; oil sands; peat; biomass; petroleum refining residues of cokes; and the like. For example, the carbon monoxide can be provided to the reaction mixture as a component of synthesis gas or "syngas", comprising carbon dioxide, carbon monoxide, and hydrogen. The hydrogen and carbon monoxide can be mixed together before the contacting, or a stream of hydrogen and a separate stream of carbon monoxide can be contacted with the alcohol.

The molar ratio of carbon monoxide to hydrogen ($CO:H_2$) can vary over a wide range. For example, $CO:H_2$, can range from 50:1 to 1:50. In other examples, $CO:H_2$ ranges from 10:1 to 1:10 or 5:1 to 1:5 or 3:1 to 1:3 or 2:1 to 1:2 or 10:1 to 1:1 or 5:1 to 1:1 or 2:1 to 1:1 or 2:1 to 1:5 or 1:1 to 1:5 or 1:1 to 1:10.

The amount of catalyst composition can be measured in terms of the moles of cobalt, the moles of phosphine ligand, the moles phosphonium iodide, the molar ratio of phosphine ligand to cobalt (phosphine ligand:cobalt), and/or the molar ratio of phosphonium iodide to cobalt (phosphonium iodide:cobalt). In one aspect, the cobalt is present in an amount ranging from 0.001 moles to 50 moles of cobalt per 100 moles of methanol. Other examples of cobalt concentration include 0.001 moles to 10 moles of cobalt per 100 moles of methanol, 0.01 moles to 5 moles of cobalt per 100 moles of methanol, 0.01 moles to 2 moles of cobalt per 100 moles of methanol, and 0.02 moles to 5 moles of cobalt per 100 moles of methanol. In one aspect, the molar ratio of the phosphine ligand to the cobalt (phosphine ligand:cobalt) ranges from 0.025:1 to 2:1. In other examples, the molar ratio of phosphine ligand to cobalt (phosphine ligand:cobalt) ranges from 0.025:1 to 0.5:1 or 0.025:1 to 1:1 or 0.025:1 to 1.5:1 or 0.1:1 to 1:1 or 0.1:1 to 0.1:1.5, or 1:1 to 2:1. In one aspect, the molar ratio of the phosphonium iodide to the cobalt (phosphonium iodide:cobalt) ranges from 0.1:1 to 50:1. In other examples, the molar ratio of phosphonium iodide to cobalt (phosphonium iodide:cobalt) ranges from 0.1:1 to 20:1 or 0.1:1 to 10:1 or 0.1:1 to 5:1 or 1:1 to 50:1 or 1:1 to 20:1 or 1:1 to 10:1 or 1:1 to 1.5:1.

For a batch reaction, the catalyst concentration can be determined based on the moles of catalyst charged per 100 moles of methanol charged to the batch reactor. For a continuous reaction, the catalyst concentration can be determined based on the moles of catalyst fed per 100 moles of methanol fed to the reactor over a given time period. The catalyst and the methanol can be fed to the reactor together or separately.

The present invention can be conducted under continuous, semi-continuous, and batch modes of operation and can utilize a variety of reactor types. The term "continuous" as used herein means a process wherein reactants are introduced and products withdrawn simultaneously in an uninterrupted manner. By "continuous" it is meant that the process is substantially or completely continuous in operation and is to be contrasted with a "batch" process. "Continuous" is not meant in any way to prohibit normal interruptions in the continuity of the process due to, for example, start-up, reactor maintenance, or scheduled shut down periods. The term "batch" process as used herein means a process wherein all the reactants are added to the reactor and then processed according to a predetermined course of reaction during which no material is fed into or removed from the reactor. The term "semicontinuous" means a process where some of the reactants are charged at the beginning of the process and the remaining reactants are fed continuously as the reaction progresses. Alternatively, a semicontinuous process may also include a process similar to a batch process in which all the reactants are added at the beginning of the process except that one or more of the products are removed continuously as the reaction progresses.

Any of the known carbonylation reactor designs or configurations may be used in carrying out the process provided by the present invention. Examples of suitable reactor types include, but are not limited to, stirred tank, continuous stirred tank, tower, and tubular reactors. The process also may be practiced in a batchwise manner by contacting the low molecular weight alcohol, hydrogen and carbon monoxide with the present catalyst composition in an autoclave.

The amount of methyl iodide in the crude reductive carbonylation product is significantly less than in typical methanol carbonylation processes. In one aspect, the crude reductive carbonylation product comprises less than 1 weight percent methyl iodide, based on the total weight of the crude reductive carbonylation product. In other aspects, the crude reductive carbonylation product comprises less than 0.8 weight percent, less than 0.5 weight percent, less than 0.1 weight percent, less than 0.05 weight percent, less than 100 ppm, less than 50 ppm, less than 10 ppm, less than 100 ppb, less than 50 ppb, or less than 10 ppb of methyl iodide, based on the total weight of the crude reductive carbonylation product.

The process can be carried out over a range of temperatures. For example, the process can be carried out at a temperature ranging from 100° C. to 250° C. In other examples, the process can be carried out at a temperature ranging from 150° C. to 230° C., or ranging from 170° C. to 210° C.

The process can be carried out over a range of pressures. For example, the process can be carried out at a pressure ranging from 100 kPa (15 psig) to 60 MPa bar (8700 psig). In other examples, the process can be carried out at a pressure ranging from 1 MPa (150 psig) to 40 MPa (5800 psig) or ranging from 6.9 MPa (1000 psig) to 34 MPA (4900 psig).

In one aspect of our invention, the contacting of the hydrogen, carbon monoxide, and methanol can occur in the presence of a solvent selected from alkanes and arenes having 6 to 20 carbon atoms, ketones having 5 to 20 carbon atoms, esters having 5 to 20 carbon atoms, ethers having 5 to 20 carbon atoms, and alkyl carbonate esters having from 3 to 20 carbon atoms. Some representative examples of the solvent include, but are not limited to, hexane, heptane, octane, decane, benzene, toluene, xylenes, methyl napththalenes, 3-methyl-2-butanone, methyl isobutyl ketone (also known as 4-methyl-2-pentanone), methyl isopropyl ketone, methyl propyl ketone, diisobutyl ketone, isobutylisobutyrate, ethyl acetate, n-butyl acetate, isobutylacetate, isopropylacetate, n-propyl acetate, diisopropylether, dibutylether, tertiary-amyl methyl ether, tertiary-butyl methyl ether, and mixtures thereof. In one aspect of our invention, the solvent can be toluene, heptane, cyclohexane, ethylbenzene, diethyl ether, 4-methylanisol, or mixtures thereof.

The amount of solvent used is not critical to the subject invention. For example, the solvent can be present in an amount ranging from 5 vol % to 90 vol % based on the total volume of solvent and alcohol. In other examples, the solvent can be present in an amount ranging from 10 vol % to 80 vol %: 20 vol % to 60 vol %: or 30 vol % to 50 vol %, each based on the total volume of solvent and methanol.

Listing of Non-Limiting Embodiments

Embodiment A is a catalyst composition comprising a complex of cobalt, iodide, and an onium cation or an alkali metal cation of the general formula $Y_2CoI_4$. Y is the onium cation or alkali metal cation. The catalyst composition also comprises a phosphine ligand of the general formula

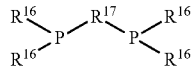

The phosphorus atoms P are bridged by 2 to 6 atoms of $R^{17}$. $R^{17}$ is selected from the group consisting of a substituted or unsubstituted alkylene, cycloalkylene, arylene, and biarylene, each having up to 22 carbon atoms. A heteroatom, optionally, can substitute for one or more of the carbon atoms. The heteroatom can be nitrogen, oxygen, sulfur, phosphorus or mixtures thereof. $R^{16}$ can be substituted or unsubstituted alkyl, alkoxy, cycloalkyl, aryl, or aryloxy, each having up to 20 carbon atoms. The catalyst composition also comprises phosphonium iodide.

The catalyst composition of Embodiment A wherein the onium cation is of the general formula (I) or (II)

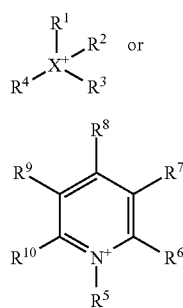

X can be phosphorus (P) or (N), $R^1$ is methyl and $R^2$, $R^3$, and $R^4$ are independently selected from alkyl having up to 12 carbons and aryl, wherein when $R^2$, $R^3$, and/or $R^4$ are aryl, each aryl is the same, and can be phenyl, tolyl, xylyl, or mesityl: or the onium cation is formula (II), $R^5$ is methyl and $R^6$, $R^7$, $R^8$, $R^9$, and $R^{10}$ are hydrogen: or the onium cation is selected from the group consisting of methyltriphenylphosphonium, methyltributylphosphonium, methyltrioctylphosphonium, and 1-methylpyridinium: or the onium cation is selected from the group consisting of methyltriphenylphosphonium and 1-methylpyridinium: or the onium cation comprises methyltriphenylphosphonium: or the alkali metal cation is selected from the group consisting of lithium, sodium, potassium, rubidium, and cesium: or the alkali metal cation is selected from the group consisting of lithium, sodium, potassium: or the complex is selected from the group consisting of bis(methyltriphenylphosphonium) cobalt tetraiodide, bis(methyltributylphosphonium) cobalt tetraiodide, bis(methyltrioctylphosphonium), and bis(1-methylpyridinium) cobalt tetraiodide.

The catalyst composition of Embodiment A or Embodiment A with one or more of the intervening features wherein the phosphine ligand is selected from the group consisting of 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and 1,3-bis(diphenylphosphino)cyclobutane: or the phosphine ligand is selected from the group consisting of 1,3-bis(diphenylphosphino)propane; 1,1,1,-tris(diphenylphosphinomethyl)ethane; and 1,1,1-tris(diethylphosphinomethyl)ethane: or the phosphine ligand comprises 1,3-bis(diphenylphosphino)propane.

The catalyst composition of Embodiment A or Embodiment A with one or more of the intervening features wherein the phosphonium iodide is selected from the group consisting of methyltriphenylphosphonium iodide, methyltributylphosphonium iodide, methyltrioctylphosphonium iodide, butyltridodecylphosphonium iodide, tetraoctylphosphonium iodide, tetrabutylphosphonium iodide, triphenyl(hexyl)phosphonium iodide, triphenyl(octyl)phosphonium iodide, tribenzyl(octyl)phosphonium iodide, tribenzyl(dodecyl)phosphonium iodide, triphenyl(decyl)phosphonium iodide, triphenyl(dodecyl)phosphonium iodide, tetra(2-methylpropyl)phosphonium iodide, tris(2-methylpropyl)-(butyl)phosphonium iodide, triphenyl(3,3-dimethylbutyl)phosphonium iodide, triphenyl(3-methylbutyl)phosphonium iodide, tris(2-methylbutyl)(3-methyl-butyl)phosphonium iodide, triphenyl[2-trimethylsilylethyl]phosphonium iodide, tris(p-chlorophenyl)(dodecyl)phosphonium iodide, hexyltris(2,4,6-trimethylphenyl)phosphonium iodide, tetradecyltris(2,4,6-trimethyl-phenyl)phosphonium iodide, dodecyltris(2,4,6-trimethylphenyl)phosphonium iodide, methyltrioctylphosphonium iodide, methyltributylphosphonium iodide, and methyltricyclohexylphosphonium iodide: or methyltriphenylphosphonium iodide, methyltributylphosphonium iodide, and methyltrioctylphosphonium iodide: or comprises methyltriphenylphosphonium iodide.

The catalyst composition of Embodiment A or Embodiment A with one or more of the intervening features wherein the molar ratio of phosphine ligand to cobalt (phosphine ligand:cobalt) ranges from 0.025:1 to 2:1 or ranges from 0.025:1 to 1:1.

The catalyst composition of Embodiment A or Embodiment A with one or more of the intervening features wherein the molar ratio of phosphonium iodide to cobalt (phosphonium iodide:cobalt) ranges from 1:1 to 50:1 or ranges from 1:1 to 20:1.

Embodiment B is a process for the preparation of a crude reductive carbonylation product comprising contacting hydrogen, carbon monoxide, and methanol in the presence of a catalyst composition to form the crude reductive carbonylation product. The crude reductive carbonylation product comprises acetaldehyde equivalents in a higher mole percent than acetic acid equivalents or ethanol equivalents, each based on the total moles of the acetaldehyde equivalents, the acetic acid equivalents, and the ethanol equivalents. The catalyst composition comprises a complex of cobalt, iodide, and an onium cation of the general formula $Y_2CoI_4$, wherein the onium cation is of the general formula (I) or (II)

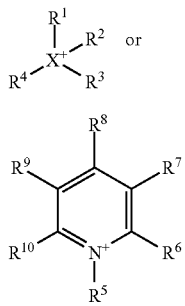

X is phosphorus (P), $R^1$ is methyl, and $R^2$, $R^3$, and $R^4$ are independently selected from alkyl having up to 12 carbons and aryl, wherein when $R^2$, $R^3$, and/or $R^4$ are aryl, each aryl is the same, and can be phenyl, tolyl, xylyl, or mesityl: or the onium cation is formula (II), $R^5$ is methyl and $R^6$, $R^7$, $R^8$, $R^9$, and $R^{10}$ are hydrogen. The catalyst composition also comprises a phosphine ligand selected from the group consisting of 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and 1,3-bis(diphenylphosphino)cyclobutane. The catalyst also comprises a phosphonium iodide. The crude reductive carbonylation product comprises less than 1 weight percent of methyl iodide.

The process of Embodiment B wherein the onium cation is selected from the group consisting of methyltriphenylphosphonium, methyltributylphosphonium, methyltrioctylphosphonium, and 1-methylpyridinium: or the onium cation is selected from the group consisting of methyltriphenylphosphonium and 1-methylpyridinium: or the complex is selected from the group consisting of bis(methyltriphenylphosphonium) cobalt tetraiodide, bis(methyltributylphosphonium) cobalt tetraiodide, bis(methyltrioctylphosphonium), and bis(1-methylpyridinium) cobalt tetraiodide.

The process of Embodiment B or Embodiment B with one or more of the intervening features wherein the phosphine ligand is selected from the group consisting of 1,3-bis(diphenylphosphino)propane; 1,1,1,-tris(diphenylphosphinomethyl)ethane; and 1,1,1-tris(diethylphosphinomethyl)ethane: or the phosphine ligand comprises 1,3-bis(diphenylphosphino)propane.

The process of Embodiment B or Embodiment B with one or more of the intervening features wherein the phosphonium iodide is selected from the group consisting of methyltriphenylphosphonium iodide, methyltributylphosphonium iodide, and methyltrioctylphosphonium iodide: or comprises methyltriphenylphosphonium iodide.

The process of Embodiment B or Embodiment B with one or more of the intervening features wherein the phosphine ligand to said cobalt (phosphine ligand:cobalt) ranges from 0.025:1 to 2:1 or ranges from 0.025:1 to 1:1.

The process of Embodiment B or Embodiment B with one or more of the intervening features wherein the molar ratio of phosphonium iodide to cobalt (phosphonium iodide:cobalt) ranges from 1:1 to 50:1 or ranges from 1:1 to 20:1.

The process of Embodiment B or Embodiment B with one or more of the intervening features wherein the crude reductive carbonylation product comprises acetaldehyde equivalents in at least 10 higher mole percent, 25 higher mole percent, 50 higher mole percent, or 75 higher mole percent than acetic acid equivalents; and acetaldehyde equivalents in at least 10 higher mole percent, 25 higher mole percent, 50 higher mole percent, or 75 higher mole percent than ethanol equivalents.

The process of Embodiment B or Embodiment B with one or more of the intervening features wherein the crude reductive carbonylation product comprises less than 1 weight percent methyl iodide: or less than 500 ppm methyl iodide: or less than 10 ppm methyl iodide.

The process of Embodiment B or Embodiment B with one or more of the intervening features wherein the cobalt is present in an amount ranging from 0.001 moles to 10 moles of the cobalt per 100 moles of methanol; or from 0.01 moles to 5 moles of cobalt per 100 moles of methanol, or from 0.02 moles to 5 moles of cobalt per 100 moles of methanol.

The process of Embodiment B or Embodiment B with one or more of the intervening features wherein the process is carried out at a temperature ranging from 100° C. to 250° C.; or from 150° C. to 230° C.

The process of Embodiment B or Embodiment B with one or more of the intervening features wherein the process is carried out at a pressure ranging from 100 kPa (15 psig) to 60 MPa (8700 psig); or from 1 MPa (150 psig) to 40 MPa (5800 psig); or from 6.9 MPa (1000 psig) to 34 MPA (4900 psig).

The process of Embodiment B or Embodiment B with one or more of the intervening features wherein the molar ratio of carbon monoxide to hydrogen, $CO:H_2$, ranges from 10:1 to 1:10 or from 5:1 to 1:5.

The process of Embodiment B or Embodiment B with one or more of the intervening features wherein the contacting further occurs in the presence of a solvent selected from the group consisting of alkanes and arenes having 6 to 20 carbon atoms, ketones having 5 to 20 carbon atoms, esters having 5 to 20 carbon atoms, ethers having 5 to 20 carbon atoms, and alkyl carbonate esters having 3 to 20 carbon atoms: or wherein the contacting further occurs in the presence of a solvent selected from the group consisting of toluene, heptane, cyclohexane, ethylbenzene, diethyl ether, and 4-methylanisole.

EXAMPLES

Abbreviations (MePPh$_3$)$_2$CoI$_4$=Bis(methyltriphenylphosphonium)cobalt tetraiodide=(CH$_3$P(C$_6$H$_5$)$_3$)$_2$CoI$_4$;
MeI=methyl iodide;
DME=dimethyl ether;
THF=tetrahydrofuran;
dppp=1,3-bis(diphenylphosphino)propane;
MePPh$_3$I=methyltriphenylphosphonium iodide=CH$_3$P(C$_6$H$_5$)$_3$I
RuO$_2$xH$_2$O=ruthenium(IV)oxide hydrate and
STY=space time yield Selectivities are reported as selectivity to acetaldehyde equivalents, acetic acid equivalents, ethanol equivalents, and C4 equivalents relative to methanol carbonylated. Reported acetaldehyde equivalents include: Acetaldehyde, Paraldehyde, Acetaldehyde dimethyl acetal, Acetaldehyde methyl ethyl acetal, Acetaldehyde diethyl acetal. Reported acetic acid equivalents include: Acetic acid, Methyl acetate, and Ethyl acetate. Reported ethanol equivalents include all ethoxy containing products including: Ethanol, Acetaldehyde diethyl acetal, Acetaldehyde methyl ethyl acetal, Diethyl ether, Methyl ethyl ether, and Ethyl acetate. Reported C4 equivalents include: n-Butyl alcohol, Crotonaldehyde, n-Butyraldehyde, Butyraldehyde acetals, and Crotyl alcohol. A summary of commonly observed products and byproducts is provided in Table 1.

TABLE 1 commonly observed products incorporated into selectivity calculations for methanol reductive carbonylation

| Ethanol Equivalents | Acetaldehyde Equivalents | Acetic Acid Equivalents | C4 Equivalents |
|---|---|---|---|
| Ethanol | Acetaldehyde | Acetic acid | n-Butyl alcohol |
| Acetaldehyde diethyl acetal | Acetaldehyde dimethyl acetal | Methyl acetate | Crotonaldehyde n-Butyraldehyde |
| Acetaldehyde methyl ethyl acetal | Acetaldehyde methyl ethyl acetal | Ethyl acetate | Butyraldehyde acetals |
| Diethyl ether | Acetaldehyde diethyl acetal | | Crotyl Alcohol |
| Methyl ethyl ether | Paraldehyde | | |
| Ethyl acetate | | | |

The phosphonium salts and ammonium salts used in these examples are easily prepared by alkylation of the parent tertiary phosphine or amine with an alkyl halide, a process well known to practitioners of the art. Complexes of the type Y$_2$CoI$_4$ where Y=MePPh$_3$ (methyltriphenylphosphonium) were prepared by the method of Wegman et al., *J. Mol. Cat.*, 32, (1985), 125-136.

Phosphine ligands, phosponium iodide, solvents, and methanol were purchased and used without further processing.

The contents of the examples were analyzed by gas chromatography. When the reaction products formed two liquid phases at room temperature, an additional component, such as THF, was added to ensure a one-phase liquid sample was fed to the gas chromatograph. Catalyst was not removed from the reaction product before analysis. Selectivities are reported based upon detection of the components listed in Table 1. The detection limit for methyl iodide (MeI) was 100 ppm. MeI listed as n/d indicates that no methyl iodide was detected.

Methanol Conversion was calculated as the difference between the initial amount of methanol and the recovered amount of free methanol divided by the initial amount of methanol. Methanol is converted to carbonylated products and non-carbonylated methoxy-containing products. As the non-carbonylated Methoxy-containing products would be readily recycled in a commercial process, the effective selectivities are based upon the moles of Methanol Carbonlyated. The moles of Methanol Carbonylated were calculated as the sum of homologated products.

Moles of Methanol Carbonylated=moles Acetaldehyde+3*moles Paraldehyde+moles Acetaldehyde dimethyl acetal+moles Acetaldehyde methyl ethyl acetal+moles Acetaldehyde diethyl acetal)+moles Acetic acid+moles Methyl acetate+moles Ethyl acetate+moles Ethanol+2*moles Acetaldehyde diethyl acetal+moles Acetaldehyde methyl ethyl acetal+2*moles Diethyl ether+moles Methyl ethyl ether+moles Ethyl acetate+2*moles n-Butyl alcohol+2*moles Crotonaldehyde+2*moles n-Butyraldehyde+2*moles Butyraldehyde acetals+2*moles Crotyl alcohol.

Selectivities to one of the product equivalents, as detailed in equations 1-4 below, are reported as the sum of methanol carbonylated to the product equivalent divided by the total amount of methanol carbonylated.

(1) % Acetaldehyde Equivalents Selectivity=100*(moles Acetaldehyde+3*moles Paraldehyde+moles Acetaldehyde dimethyl acetal+moles Acetaldehyde methyl ethyl acetal+moles Acetaldehyde diethyl acetal)/moles Methanol Carbonylated (2) % Acetic Acid Equivalents Selectivity=100*(moles Acetic acid+moles Methyl acetate+moles Ethyl acetate)/moles Methanol Carbonylated (3) % Ethanol Equivalents Selectivity=100*(moles Ethanol+2*moles Acetaldehyde diethyl acetal+moles Acetaldehyde methyl ethyl acetal+2*moles Diethyl ether+moles Methyl ethyl ether+moles Ethyl acetate)/moles Methanol Carbonylated (4) % C4 Equivalents Selectivity=100*(2*moles n-Butyl alcohol+2*moles Crotonaldehyde+2*moles n-Butyraldehyde+2*moles Butyraldehyde acetals+2*moles Crotyl alcohol)/moles Methanol Carbonylated.

Yield of Carbonylated Products was calculated as the Moles of Methanol Carbonylated divided by the initial amount of methanol.

Space Time Yield (STY), for a methanol feed and with acetaldehyde equivalents as the desired product, was calculated as the moles of acetaldehyde equivalents produced per liter of initial reaction mixture per hours of reaction (moles per liter per hour, Mh$^{-1}$).

Mole percent (Mole %) of methyl iodide (MeI) or dimethyl ether (DME) were calculated as the percentage of moles of species produced compared to the initial amount of methanol charged to the reactor.

Example 1

A 100-mL Hastelloy® C autoclave was charged with a solution of (MePPh$_3$)$_2$CoI$_4$ (0.309 mmol), MePPh$_3$I (0.618 mmol), dppp (0.309 mmol) in 50 mL of methanol, sealed and purged 3 times with N$_2$. The reactor was pressurized to 6.9 MPa (1000 psig) with 1:1 CO:H$_2$ and heated to 195° C. Upon reaching 195° C., the reactor was pressurized to a total pressure of 27.6 MPa (4000 psig) with 1:1 CO:H$_2$. After 30 minutes the reactor was cooled to 5° C. and the gas was vented. The contents were analyzed by gas chromatography and the results are shown in Table 2.

Examples 2-9 and Comparative Example C1

Example 1 was repeated except the amount of phosphonium iodide was as given in Table 2. Example 8 was a duplicate of Example 7 with the other examples varying the amount phosphonium iodide. Comparative Example C1 was run without any phosphonium iodide. While Comparative Example C1 shows a comparable Space Time Yield to Examples 1-4, all of the Examples in Table 2 show an improvement in STY or an improvement in selectivity to acetaldehyde equivalents upon addition of phosphonium iodide. Examples 1-9 and Comparative Example C1 show no detectable methyl iodide and 0.8 mol % as the highest level of DME.

sure of 27.6 MPa (4000 psig) with 1:1 $CO:H_2$. After 30 minutes the reactor was cooled to 5° C. and the gas was vented. The contents were analyzed by gas chromatography and the results are shown in Table 4. Example 15 was a duplicate of example 14. Examples 14-15 show no detectable methyl iodide and 0.7 mol % as the highest level of DME

Examples 16-17

Example 14 was repeated except a solvent was used at a 50 vol % level. Example 17 is a repeat of Example 16. The solvent used and the amount of catalyst, as well as the results are given in Table 4. One skilled in the art would recognize

TABLE 2

Reductive carbonylation of methanol to acetaldehyde equivalents at 195° C., 4000 psig, carbon monoxide to hydrogen ratio of 1:1 for 30 minutes.

| Ex | $(MePPh_3)_2CoI_4$ (mole % relative to Methanol) | dppp (mole % relative to Methanol) | $MePPh_3I$ (mole % relative to methanol) | Methanol Conversion | Yield of Carbonylated Products | Acetaldehyde Selectivity | Ethanol Selectivity | Acetic Acid Selectivity | C4 Selectivity | STY $(Mh^{-1})$ | Mol % DME in product |
|---|---|---|---|---|---|---|---|---|---|---|---|
| 1 | 0.025% | 0.025% | 0.05% | 60% | 23% | 86 | 5 | 7 | 3 | 9.9 | 0.7% |
| 2 | 0.025% | 0.025% | 0.10% | 61% | 25% | 86 | 5 | 6 | 3 | 10.8 | 0.8% |
| 3 | 0.025% | 0.025% | 0.15% | 61% | 24% | 88 | 3 | 7 | 1 | 10.5 | 0.7% |
| 4 | 0.025% | 0.025% | 0.20% | 58% | 21% | 89 | 3 | 6 | 2 | 9.2 | 0.6% |
| 5 | 0.025% | 0.025% | 0.25% | 72% | 31% | 83 | 2 | 12 | 3 | 12.7 | 0.6% |
| 6 | 0.025% | 0.025% | 0.30% | 71% | 32% | 82 | 2 | 12 | 3 | 13.2 | 0.7% |
| 7 | 0.025% | 0.025% | 0.35% | 71% | 32% | 82 | 2 | 13 | 3 | 13.2 | 0.7% |
| 8 | 0.025% | 0.025% | 0.35% | 72% | 39% | 80 | 2 | 15 | 3 | 15.3 | 0.7% |
| 9 | 0.025% | 0.025% | 0.40% | 72% | 33% | 83 | 2 | 13 | 2 | 13.4 | 0.7% |
| C1 | 0.025% | 0.025% | 0.00% | 66% | 27% | 81 | 7 | 9 | 3 | 10.9 | 0.7% |

Examples 10-13

Example 7 was repeated except the amount of dppp as given in Table 3. Example 11 was a duplicate of Example 12 with the other examples varying the amount dppp. Examples 10-13 show no detectable methyl iodide and 0.8 mol % as the highest level of DME.

that the Space Time Yield would be lower for systems with 50 vol % solvent compared to systems with no solvent. For example, comparing Examples 14 and 16 which were run under the same conditions except that Example 16 had 50 vol % toluene, the STY for Example 14 was 14.0 while the STY for Example 16 was 3.2. The use of solvent does, however, improve selectivity to acetaldehyde equivalents. For Example

TABLE 3

Reductive carbonylation of methanol to acetaldehyde equivalents at 195° C., 4000 psig, carbon monoxide to hydrogen ratio of 1:1 for 30 minutes.

| Ex | $(MePPh_3)_2CoI_4$ (mole % relative to Methanol) | dppp (mole % relative to Methanol) | $MePPh_3I$ (mole % relative to methanol) | Methanol Conversion | Yield of Carbonylated Products | Acetaldehyde Selectivity | Ethanol Selectivity | Acetic Acid Selectivity | C4 Selectivity | STY $(Mh^{-1})$ | Mol % DME in product |
|---|---|---|---|---|---|---|---|---|---|---|---|
| 10 | 0.025% | 0.002% | 0.35% | 66% | 30% | 83 | 1 | 14 | 2 | 12.2 | 0.7% |
| 11 | 0.025% | 0.012% | 0.35% | 67% | 31% | 83 | 1 | 14 | 2 | 12.6 | 0.8% |
| 12 | 0.025% | 0.012% | 0.35% | 74% | 38% | 78 | 3 | 14 | 5 | 14.6 | 0.7% |
| 13 | 0.025% | 0.038% | 0.35% | 74% | 35% | 79 | 3 | 14 | 4 | 13.9 | 0.5% |

Examples 14-15

A 100-mL Hastelloy® C autoclave was charged with a solution of $(MePPh_3)_2CoI_4$ (0.309 mmol), $MePPh_3I$ (4.94 mmol), DPPP (0.309 mmol) in 25 mL of methanol, sealed and purged 3 times with $N_2$. The reactor was pressurized to 6.9 MPa (1000 psig) with 1:1 $CO:H_2$ and heated to 195° C. Upon reaching 195° C., the reactor was pressurized to a total pres- 14, the selectivity to acetaldehyde equivalents was 84% compared to 92% for Example 16. Each of Examples 16 and 17 produced products which separated into two distinct liquid phases at room temperature. Advantageously, the catalyst which would be recycled in a continuous process partitioned to the aqueous phase, while the desired products partitioned to the organic phase. Examples 16-17 show no detectable methyl iodide and 0.3 mol % as the highest level of DME

TABLE 4

Reductive carbonylation of methanol to acetaldehyde equivalents at 195° C., 4000 psig, carbon monoxide to hydrogen ratio of 1:1 for 30 minutes.

| Ex | (MePPh$_3$)$_2$CoI$_4$ (mole % relative to Methanol) | dppp (mole % relative to Methanol) | MePPh$_3$I (mole % relative to methanol) | Solvent | Methanol Conversion | Yield of Carbonylated Products | Acetal-dehyde Selectivity | Ethanol Selectivity | Acetic Acid Selectivity | C4 Selectivity | STY (Mh$^{-1}$) | Mol % DME in product |
|---|---|---|---|---|---|---|---|---|---|---|---|---|
| 14 | 0.05% | 0.05% | 0.799% | — | 71% | 33% | 84 | 4 | 8 | 3 | 14.0 | 0.6% |
| 15 | 0.05% | 0.05% | 0.799% | — | 74% | 41% | 81 | 2 | 14 | 4 | 17.5 | 0.7% |
| 16 | 0.05% | 0.05% | 0.799% | Toluene | 60% | 17% | 92 | 1 | 5 | 2 | 3.8 | 0.2% |
| 17 | 0.05% | 0.05% | 0.799% | Toluene | 69% | 25% | 85 | 1 | 8 | 7 | 5.8 | 0.3% |

Examples 18-20

Example 7 was repeated except the temperature was varied as given in Table 5. These Examples show that increasing reaction temperature leads to an increase in reaction rate at comparable selectivity to acetaldehyde equivalents. Examples 18-20 show no detectable methyl iodide and 0.8 mol % as the highest level of DME.

TABLE 5

Reductive carbonylation of methanol to acetaldehyde equivalents at 4000 psig, carbon monoxide to hydrogen ratio of 1:1 for 30 minutes.

| Ex | (MePPh$_3$)$_2$CoI$_4$ (mole % relative to Methanol) | dppp (mole % relative to Methanol) | MePPh$_3$I (mole % relative to methanol) | Temp ° C. | Methanol Conversion | Yield of Carbonylated Products | Acetal-dehyde Selectivity | Ethanol Selectivity | Acetic Acid Selectivity | C4 Selectivity | STY (Mh$^{-1}$) | Mol % DME in product |
|---|---|---|---|---|---|---|---|---|---|---|---|---|
| 18 | 0.025% | 0.025% | 0.35% | 175 | 62% | 28% | 79 | 1 | 18 | 2 | 10.9 | 0.6% |
| 19 | 0.025% | 0.025% | 0.35% | 185 | 67% | 33% | 80 | 2 | 16 | 2 | 13.1 | 0.6% |
| 20 | 0.025% | 0.025% | 0.35% | 205 | 71% | 37% | 79 | 2 | 15 | 3 | 14.4 | 0.8% |

Examples 21-38 and Comparative Examples C2-C4

Example 7 was repeated except the pressure was reduced to 3000 or 2000 psig, molar ratio of carbon monoxide to hydrogen CO:H$_2$ was 1:1 and the amount of dppp was varied as given in Table 6. Example 22 was a duplicate of Example 21, Example 24 was a duplicate of Example 23, Examples 26 and 27 were duplicates of Example 25, Example 30 was a duplicate of Example 29, Example 32 was a duplicate of Example 31, Example 34 was a duplicate of Example 33, and Examples 36, 37 and 38 were duplicates of Example 35. These Examples show that varying the amount of ligand has an effect on reaction rate. Examples 21-38 show no detectable methyl iodide and 0.6 mol % as the highest level of DME. Comparative Examples C2-C4 were run with no ligand and/or no phosphonium iodide and had a STY ranging from 6.3-6.5, whereas Examples 21-28 were run at the same conditions except with ligand and phosphonium iodide and had a STY ranging from 8.7-11.5.

TABLE 6

Reductive carbonylation of methanol to acetaldehyde equivalents at 195° C., carbon monoxide to hydrogen ratio of 1:1 for 30 minutes.

| Ex | (MePPh$_3$)$_2$CoI$_4$ (mole % relative to Methanol) | dppp (mole % relative to Methanol) | MePPh$_3$I (mole % relative to methanol) | Pressure (psig) 1:1 CO:H$_2$ | Methanol Conversion | Yield of Carbonylated Products | Acetal-dehyde Selectivity | Ethanol Selectivity | Acetic Acid Selectivity | C4 Selectivity | STY (Mh$^{-1}$) | Mol % DME in product |
|---|---|---|---|---|---|---|---|---|---|---|---|---|
| 21 | 0.025% | 0.002% | 0.35% | 3000 | 60% | 20% | 84 | 1 | 13 | 2 | 8.3 | 0.5% |
| 22 | 0.025% | 0.002% | 0.35% | 3000 | 53% | 21% | 85 | 1 | 13 | 1 | 8.8 | 0.6% |
| 23 | 0.025% | 0.012% | 0.35% | 3000 | 61% | 22% | 83 | 2 | 13 | 2 | 9.1 | 0.5% |
| 24 | 0.025% | 0.012% | 0.35% | 3000 | 60% | 25% | 84 | 2 | 13 | 2 | 10.4 | 0.6% |
| 25 | 0.025% | 0.025% | 0.35% | 3000 | 58% | 21% | 84 | 2 | 12 | 2 | 8.7 | 0.5% |
| 26 | 0.025% | 0.025% | 0.35% | 3000 | 70% | 27% | 81 | 2 | 14 | 3 | 10.7 | 0.5% |
| 27 | 0.025% | 0.025% | 0.35% | 3000 | 62% | 28% | 82 | 2 | 14 | 2 | 11.2 | 0.6% |

TABLE 6-continued

Reductive carbonylation of methanol to acetaldehyde equivalents at 195° C., carbon monoxide to hydrogen ratio of 1:1 for 30 minutes.

| Ex | (MePPh$_3$)$_2$CoI$_4$ (mole % relative to Methanol) | dppp (mole % relative to Methanol) | MePPh$_3$I (mole % relative to methanol) | Pressure (psig) 1:1 CO:H$_2$ | Methanol Conversion | Yield of Carbonylated Products | Acetaldehyde Selectivity | Ethanol Selectivity | Acetic Acid Selectivity | C4 Selectivity | STY (Mh$^{-1}$) | Mol % DME in product |
|---|---|---|---|---|---|---|---|---|---|---|---|---|
| 28 | 0.025% | 0.038% | 0.35% | 3000 | 63% | 28% | 83 | 2 | 14 | 2 | 11.5 | 0.6% |
| C2 | 0.025% | — | — | 3000 | 42% | 15% | 85 | 3 | 9 | 3 | 6.3 | 0.4% |
| C3 | 0.025% | 0.025% | — | 3000 | 45% | 16% | 85 | 4 | 9 | 3 | 6.5 | 0.4% |
| C4 | 0.025% | — | 0.35% | 3000 | 49% | 15% | 85 | 1 | 12 | 1 | 6.5 | 0.5% |
| 29 | 0.025% | 0.002% | 0.35% | 2000 | 26% | 9% | 85 | 1 | 13 | 1 | 3.8 | 0.4% |
| 30 | 0.025% | 0.002% | 0.35% | 2000 | 38% | 11% | 79 | 1 | 14 | 6 | 4.3 | 0.3% |
| 31 | 0.025% | 0.012% | 0.35% | 2000 | 23% | 8% | 85 | 1 | 13 | 1 | 3.4 | 0.3% |
| 32 | 0.025% | 0.012% | 0.35% | 2000 | 37% | 12% | 80 | 1 | 14 | 5 | 4.7 | 0.4% |
| 33 | 0.025% | 0.025% | 0.35% | 2000 | 46% | 11% | 80 | 1 | 14 | 5 | 4.5 | 0.5% |
| 34 | 0.025% | 0.025% | 0.35% | 2000 | 38% | 13% | 84 | 1 | 14 | 1 | 5.5 | 0.5% |
| 35 | 0.025% | 0.038% | 0.35% | 2000 | 47% | 17% | 80 | 1 | 15 | 3 | 6.9 | 0.5% |
| 36 | 0.025% | 0.038% | 0.35% | 2000 | 41% | 15% | 84 | 1 | 14 | 1 | 6.2 | 0.5% |
| 37 | 0.025% | 0.038% | 0.35% | 2000 | 51% | 14% | 83 | 1 | 15 | 1 | 5.7 | 0.4% |
| 38 | 0.025% | 0.038% | 0.35% | 2000 | 47% | 16% | 79 | 2 | 18 | 1 | 6.2 | 0.4% |

Examples 39-47

Examples 28 and 35 were repeated except the pressure and temperature were varied as given in Table 7. Example 40 was a duplicate of Example 39, Example 43 was a duplicate of Example 42, and Example 46 was a duplicate of Example 45. Examples 39-47 show the effect of varying temperature and pressure on STY and selectivity to acetaldehyde equivalents. Examples 39-47 show no detectable methyl iodide and 0.6 mol % as the highest level of DME.

TABLE 7

Reductive carbonylation of methanol to acetaldehyde equivalents at carbon monoxide to hydrogen ratio of 1:1 for 30 minutes.

| Ex | (MePPh$_3$)$_2$CoI$_4$ (mole % relative to Methanol) | dppp (mole % relative to Methanol) | MePPh$_3$I (mole % relative to methanol) | Temp. | Pressure (psig) 1:1 CO:H$_2$ | Methanol Conversion | Yield of Carbonylated Products | Acetaldehyde Selectivity | Ethanol Selectivity | Acetic Acid Selectivity | C4 Selectivity | STY (Mh$^{-1}$) | Mol % DME in product |
|---|---|---|---|---|---|---|---|---|---|---|---|---|---|
| 39 | 0.025% | 0.038% | 0.35% | 175 | 2000 | 36% | 10% | 80 | 1 | 18 | 1 | 3.8 | 0.2% |
| 40 | 0.025% | 0.038% | 0.35% | 175 | 2000 | 37% | 12% | 76 | 1 | 22 | 1 | 4.4 | 0.2% |
| 41 | 0.025% | 0.038% | 0.35% | 175 | 3000 | 52% | 18% | 76 | 1 | 21 | 1 | 6.9 | 0.3% |
| 42 | 0.025% | 0.038% | 0.35% | 185 | 2000 | 52% | 17% | 82 | 1 | 16 | 1 | 6.9 | 0.3% |
| 43 | 0.025% | 0.038% | 0.35% | 185 | 2000 | 40% | 14% | 79 | 1 | 18 | 1 | 5.4 | 0.3% |
| 44 | 0.025% | 0.038% | 0.35% | 185 | 3000 | 66% | 30% | 78 | 2 | 18 | 2 | 11.5 | 0.6% |
| 45 | 0.025% | 0.038% | 0.35% | 205 | 2000 | 36% | 11% | 85 | 1 | 13 | 1 | 4.5 | 0.4% |
| 46 | 0.025% | 0.038% | 0.35% | 205 | 2000 | 44% | 14% | 81 | 2 | 16 | 2 | 5.7 | 0.4% |
| 47 | 0.025% | 0.038% | 0.35% | 205 | 3000 | 68% | 30% | 78 | 2 | 16 | 3 | 11.5 | 0.8% |

Examples 48-51 and Comparative Examples C5-C7

Example 7 was repeated except the molar ratio of carbon monoxide to hydrogen was changed to 1:2 CO:H$_2$ and the amount of dppp was varied is as given in Table 8. These examples show the increase in selectivity to acetaldehyde equivalents with CO:H$_2$ of 1:2 as compared to CO:H$_2$ of 1:1 and that varying the amount of ligand has an effect on STY. Examples 48-51 show no detectable methyl iodide and 0.8 mol % as the highest level of DME. Comparative Examples C5-C7 were run with no ligand and/or no phosphonium iodide and had a STY ranging from 6.6-8.0, whereas Example 50 which was run at the same conditions except with both ligand and phosphonium iodide in the amount of C5-C7 had a STY of 9.7.

TABLE 8

Reductive carbonylation of methanol to acetaldehyde equivalents at 195° C., 4000 psig, carbon monoxide to hydrogen ratio of 1:2 for 30 minutes.

| Ex | (MePPh$_3$)$_2$CoI$_4$ (mole % relative to Methanol) | dppp (mole % relative to Methanol) | MePPh$_3$I (mole % relative to methanol) | Methanol Conversion | Yield of Carbonylated Products | Acetaldehyde Selectivity | Ethanol Selectivity | Acetic Acid Selectivity | C4 Selectivity | STY (Mh$^{-1}$) | Mol % DME in product |
|---|---|---|---|---|---|---|---|---|---|---|---|
| 48 | 0.025% | 0.002% | 0.35% | 56% | 15% | 91 | 2 | 6 | 1 | 6.8 | 0.5% |
| 49 | 0.025% | 0.012% | 0.35% | 57% | 20% | 90 | 2 | 6 | 2 | 9.0 | 0.7% |
| 50 | 0.025% | 0.025% | 0.35% | 64% | 22% | 88 | 3 | 7 | 2 | 9.7 | 0.6% |
| 51 | 0.025% | 0.038% | 0.35% | 65% | 23% | 88 | 3 | 6 | 2 | 10.1 | 0.6% |
| C5 | 0.025% | 0.025% | — | 49% | 15% | 90 | 4 | 4 | 2 | 6.6 | 0.8% |
| C6 | 0.025% | — | 0.35% | 51% | 18% | 90 | 2 | 7 | 2 | 8.0 | 0.6% |
| C7 | 0.025% | — | — | 46% | 14% | 91 | 3 | 4 | 2 | 6.5 | 0.7% |

Comparative Example C8

A 100-mL Hastelloy® C autoclave was charged with a solution of (MePPh$_3$)$_2$CoI$_4$ (1.236 mmol), DPPP (0.618 mmol) in 25 mL of methanol, sealed and purged 3 times with N$_2$. The reactor was pressurized to 6.9 MPa (1000 psig) with 1:1 CO:H$_2$ and heated to 195° C. Upon reaching 195° C., the reactor was pressurized to a total pressure of 16.5 MPa (2400 psig) with 1:1 CO:H$_2$. After 30 minutes the reactor was cooled to 5° C. and the gas was vented. The contents were analyzed by gas chromatography and the results are shown in Table 9.

Examples 52-57

Comparative Example C8 was repeated except the amount of cobalt catalyst, ligand, and phosphonium iodide was as given in Table 9. In Comparative Example C8 and Examples 52-57 the total amount of phosphonium ion (defined as the amount of phosphonium in the complex of cobalt, iodide, and onium cation plus the amount of phosphonium in the phosphonium iodide salt) was held constant. The total amount of phosphonium ion in these Examples is 0.4% (in Comparative Example C8 all of the phosphonium is in the complex and in Example 57, 0.1% of the phosphonium ion is in the complex and 0.3% of the phosphonium ion is in the phosphonium iodide salt). Also, as the amount of the cobalt containing complex was reduced, the phosphine ligand was reduced to maintain a constant phosphine ligand to cobalt ratio of 0.5. Comparative Example C8 and Examples 52-57 show that the level of cobalt catalyst can be lowered without significantly lowering the reaction rate by maintaining a constant amount of phosphonium ion. Comparative Example C8 and Examples 52-57 show no detectable methyl iodide and 1.0 mol % as the highest level of DME.

TABLE 9

Reductive carbonylation of methanol to acetaldehyde equivalents at 195° C., 2400 psig, carbon monoxide to hydrogen ratio of 1:1 for 30 minutes.

| Ex | (MePPh$_3$)$_2$CoI$_4$ (mole % relative to Methanol) | dppp (mole % relative to Methanol) | MePPh$_3$I (mole % relative to methanol) | Methanol Conversion | Yield of Carbonylated Products |
|---|---|---|---|---|---|
| C8 | 0.200% | 0.100% | — | 73% | 33% |
| 52 | 0.175% | 0.088% | 0.050% | 72% | 32% |
| 53 | 0.150% | 0.075% | 0.100% | 73% | 39% |
| 54 | 0.125% | 0.063% | 0.150% | 70% | 34% |
| 55 | 0.100% | 0.050% | 0.200% | 70% | 29% |
| 56 | 0.075% | 0.038% | 0.250% | 69% | 28% |
| 57 | 0.050% | 0.025% | 0.300% | 63% | 25% |

| Ex | Acetaldehyde Selectivity | Ethanol Selectivity | Acetic Acid Selectivity | C4 Selectivity | STY (Mh$^{-1}$) | Mol % DME in product |
|---|---|---|---|---|---|---|
| C8 | 71 | 6 | 17 | 6 | 11.6 | 0.9% |
| 52 | 73 | 5 | 17 | 5 | 11.6 | 1.0% |
| 53 | 73 | 5 | 16 | 5 | 12.5 | 1.0% |
| 54 | 75 | 4 | 16 | 4 | 12.1 | 0.8% |
| 55 | 77 | 3 | 16 | 4 | 11.0 | 0.7% |
| 56 | 78 | 3 | 16 | 4 | 10.7 | 0.6% |
| 57 | 81 | 2 | 14 | 3 | 10.0 | 0.6% |

Example 59

A 100-mL Hastelloy® C autoclave was charged with a solution of (MePPh$_3$)$_2$CoI$_4$ (0.154 mmol), DPPP (0.154 mmol), MePPh$_3$I (2.472 mmol), RuO$_2$xH$_2$O (0.116 mmol) in 25 mL of methanol, sealed and purged 3 times with N$_2$. The reactor was pressurized to 6.9 MPa (1000 psig) with 1:1 CO:H$_2$ and heated to 195° C. Upon reaching 195° C., the reactor was pressurized to a total pressure of 27.6 MPa (4000 psig) with 1:1 CO:H$_2$. After 60 minutes the reactor was cooled to 5° C. and the gas was vented. The contents were analyzed by gas chromatography and the results are shown in Table 10. No methyl iodide was detected an Example 59.

TABLE 10

Reductive carbonylation of methanol to acetaldehyde equivalents at 195° C., 4000 psig, carbon monoxide to hydrogen ratio of 1:1 for 60 minutes.

| Ex | (MePPh$_3$)$_2$CoI$_4$ (mole % relative to Methanol) | DPPP (mole % relative to Methanol) | MePPh$_3$I (mole % relative to methanol) | RuO$_2$xH$_2$O (mole % relative to methanol) | Methanol Conversion | Yield of Carbonylated Products | Acetaldehyde Selectivity | Ethanol Selectivity | Acetic Acid Selectivity | C4 Selectivity | STY (Mh$^{-1}$) | Mol % DME in product |
|---|---|---|---|---|---|---|---|---|---|---|---|---|
| 59 | 0.025% | 0.025% | 0.400% | 0.019% | 66% | 34% | 39 | 51 | 6 | 4 | 1.9 | 0.5% |

The invention has been described in detail with particular reference to preferred embodiments thereof, but it will be understood that variations and modifications can be effected within the spirit and scope of the invention.

We claim:

1. A catalyst composition comprising:

a complex of cobalt, iodide, and an onium cation or an alkali metal cation of the general formula Y$_2$CoI$_4$, wherein Y is said onium cation or said alkali metal cation: and a phosphine ligand of the general formula

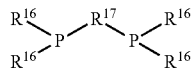

wherein phosphorus atoms P are bridged by 3 atoms of R$^{17}$, wherein R$^{17}$ is selected from the group consisting of substituted or unsubstituted alkylene, cycloalkylene, arylene, and biarylene, each having up to 22 carbon atoms; wherein a heteroatom, optionally, can substitute for one or more of said carbon atoms, wherein said heteroatom is selected from the group consisting of nitrogen, oxygen, sulfur, and phosphorus; and R$^{16}$ is selected from the group consisting of substituted or unsubstituted alkyl, alkoxy, cycloalkyl, aryl, and aryloxy, each having up to 20 carbon atoms; and a phosphonium iodide, wherein said phosphonium iodide is selected from the group consisting of methyltriphenylphosphonium iodide, methyltributylphosphonium iodide, methyltrioctylphosphonium iodide, butyltridodecylphosphonium iodide, tetraoctylphosphonium iodide, tetrabutylphosphonium iodide, triphenyl(hexyl)phosphonium iodide, triphenyl(octyl)phosphonium iodide, tribenzyl(octyl)phosphonium iodide, tribenzyl(dodecyl)phosphonium iodide, triphenyl(decyl)phosphonium iodide, triphenyl(dodecyl)phosphonium iodide, tetrakis(2-methylpropyl)phosphonium iodide, tris(2-methylpropyl)-(butyl)phosphonium iodide, triphenyl(3,3-dimethylbutyl)phosphonium iodide, triphenyl(3-methylbutyl)phosphonium iodide, tris(2-methylbutyl)(3-methyl-butyl)phosphonium iodide, triphenyl[2-trimethylsilylethyl]phosphonium iodide, tris(p-chlorophenyl)(dodecyl)phosphonium iodide, hexyltris(2,4,6-trimethylphenyl)phosphonium iodide, tetradecyltris(2,4,6-trimethyl-phenyl)phosphonium iodide, dodecyltris(2,4,6-trimethylphenyl)phosphonium iodide, methyltrioctylphosphonium iodide, methyltributylphosphonium iodide, and methyltricyclohexylphosphonium iodide.

2. The catalyst composition according to claim 1, wherein said onium cation is of the general formula (I) or (II):

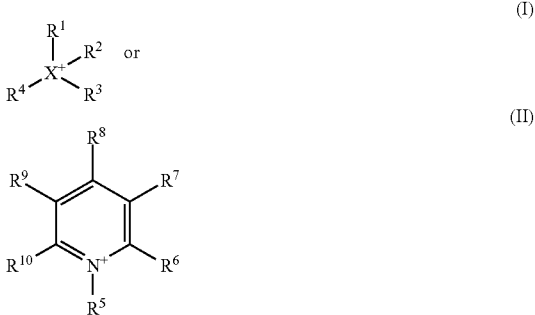

wherein X is phosphorus (P), R$^1$ is methyl, and R$^2$, R$^3$, and R$^4$ are independently selected from alkyl having up to 12 carbon atoms and aryl, wherein said aryl is selected from only one of the group consisting of phenyl, tolyl, xylyl, and mesityl; R$^5$ is methyl and R$^6$, R$^7$, R$^8$, R$^9$, and R$^{10}$ are hydrogen.

3. The catalyst composition according to claim 1, wherein said onium cation is selected from the group consisting of methyltriphenylphosphonium, methyltributylphosphonium, methyltrioctylphosphonium, and 1-methylpyridinium; and wherein said phosphine ligand is selected from the group consisting of 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and 1,3-bis(diphenylphosphino)cyclobutane.

4. The catalyst composition according to claim 1, wherein said onium cation comprises methyltriphenylphosphonium; said phosphine ligand is selected from the group consisting of 1,3-bis(diphenylphosphino)propane and 1,1,1-tris(diphenylphosphinomethyl)ethane, and 1,1,1-tris(diethylphosphinomethyl)ethane; and said phosphonium iodide is selected from the group consisting of methyltriphenylphosphonium iodide, methyltributylphosphonium iodide, and methyltrioctylphosphonium iodide.

5. The catalyst composition according to claim 1, wherein the molar ratio of said phosphine ligand to said cobalt (phosphine ligand:cobalt) ranges from 0.025:1 to 2:1 and the molar ratio of said phosphonium iodide to cobalt (phosphonium iodide:cobalt) ranges from 0.1:1 to 50:1.

6. The catalyst composition according to claim 1, wherein said onium cation comprises methyltriphenylphosphonium, said phosphine ligand comprises 1,3-bis(diphenylphosphino)propane, and said phosphonium iodide comprises methyltriphenylphosphonium iodide, and wherein the molar ratio of said phosphine ligand to said cobalt (phosphine ligand:cobalt) ranges from 0.025:1 to 1:1 and the molar ratio of said phosphonium iodide to cobalt (phosphonium iodide:cobalt) ranges from 0.1:1 to 20:1.

7. A process for the preparation of a crude reductive carbonylation product comprising contacting hydrogen, carbon monoxide, and methanol in the presence of a catalyst composition to form said crude reductive carbonylation product comprising acetaldehyde equivalents in a higher mole percent than acetic acid equivalents or ethanol equivalents, each based on the total moles of said acetaldehyde equivalents, said acetic acid equivalents, and said ethanol equivalents:

wherein said catalyst composition comprises a complex of cobalt, iodide, and an onium cation of the general formula $Y_2CoI_4$, wherein Y is said onium cation of the general formula (I) or (II)

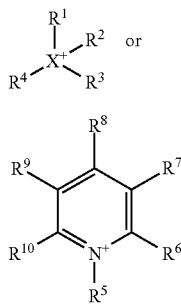

wherein X is phosphorus (P), $R^1$ is methyl, and $R^2$, $R^3$, and $R^4$ are independently selected from alkyl having up to 12 carbon atoms and aryl, wherein said aryl is selected from only one of the group consisting of phenyl, tolyl, xylyl, and mesityl; $R^5$ is methyl and $R^6$, $R^7$, $R^8$, $R^9$, and $R^{10}$ are hydrogen;

and a phosphine ligand selected from the group consisting of 1,3-bis(diphenylphosphino)propane; 1,1,1-tris(diphenylphosphinomethyl)ethane; 1,1,1-tris(diethylphosphinomethyl)ethane; 1,3-bis(dicyclohexylphosphino)propane; 1,3-bis(dimethylphosphino)propane; 1,3-bis(diisopropylphosphino)propane; 1,3-bis(di-tert-butylphosphino)propane; (2-butoxy-2-((diphenylphosphino)methyl)propane-1,3-diyl)bis(diphenylphosphine); 1,8-bis(diphenylphosphino)naphthalene; bicyclo[2.2.1]heptane-2,7-diylbis(diphenylphosphine); 1,3-bis(diphenylphosphino)cyclohexane; 1,3-bis(diphenylphosphino)cyclopentane; and 1,3-bis(diphenylphosphino)cyclobutane; and a phosphonium iodide, wherein said crude reductive carbonylation product comprises less than 1 weight percent of methyl iodide, based on the total weight of said crude reductive carbonylation product.

8. The process according to claim 7, wherein said phosphine ligand is selected from the group consisting of 1,3-bis(diphenylphosphino)propane; 1,1,1-tris(diphenylphosphinomethyl)ethane; and 1,1,1-tris(diethylphosphinomethyl)ethane; and said phosphonium iodide is selected from the group consisting of methyltriphenylphosphonium iodide, methyltributylphosphonium iodide, and methyltrioctylphosphonium iodide.

9. The process according to claim 7, wherein said onium cation comprises methyltriphenylphosphonium; said phosphine ligand comprises 1,3-bis(diphenylphosphino)propane; and said phosphonium iodide comprises methyltriphenylphosphonium iodide.

10. The process according to claim 7, wherein said cobalt is present in an amount ranging from 0.02 moles to 5 moles of said cobalt per 100 moles of said methanol, the mole ratio of said phosphine ligand to said cobalt (phosphine ligand:cobalt) ranges from 0.025:1 to 2:1, and the mole ratio of said phosphonium iodide to said cobalt (phosphonium iodide:cobalt) ranges from 1:1 to 20:1.

11. The process according to claim 7, wherein the molar ratio of said carbon monoxide to said hydrogen, CO:H2, ranges from 10:1 to 1:10.

12. The process according to claim 7, wherein the molar ratio of said carbon monoxide to said hydrogen, CO:H2, ranges from 5:1 to 1:5.

13. The process according to claim 7, wherein said process is carried out at a temperature ranging from 100° C. to 250° C. and at a pressure ranging from 100 kPa (15 psig) to 60 MPa (8700 psig).

14. The process according to claim 7, wherein said process is carried out at a temperature ranging from 150° C. to 230° C. and at a pressure ranging from 1 MPa (150 psig) to 40 MPa (5800 psig).

15. The process according to claim 7, wherein said contacting further occurs in the presence of a solvent selected the group consisting of alkanes and arenes having 6 to 20 carbon atoms, ketones having 5 to 20 carbon atoms, esters having 5 to 20 carbon atoms, ethers having 5 to 20 carbon atoms, and alky carbonate esters having 3 to 20 carbon atoms.

16. The process according to claim 7, wherein the $CO:H_2$ molar ratio ranges from 5:1 to 1:5, said process is carried out at a temperature ranging from 100° C. to 250° C. and a pressure ranging from 100 kPa (15 psig) to 60 MPa (8700 psig), and wherein said crude reductive carbonylation product comprises acetaldehyde equivalents in a higher mole percent than acetic acid equivalents or ethanol equivalents, each based on the total moles of acetaldehyde equivalents, acetic acid equivalents, and ethanol equivalents.

* * * * *